United States Patent
Wei

(10) Patent No.: US 10,874,716 B2
(45) Date of Patent: Dec. 29, 2020

(54) METHODS AND COMPOSITIONS FOR TREATMENT OF BONE, SKIN, SUBCUTANEOUS, MUCOSAL AND/OR SUBMUCOSAL CANCER BY PERCUTANEOUS AND/OR TRANSMUCOSAL ADMINISTRATION OF INTERFERON

(71) Applicant: SUPERLAB FAR EAST LIMITED, Tortola (VG)

(72) Inventor: Guangwen Wei, Chengdu (CN)

(73) Assignee: SUPERLAB FAR EAST LIMITED, Tortola (VG)

( * ) Notice: Subject to any disclaimer, the term of this patent is extended or adjusted under 35 U.S.C. 154(b) by 0 days.

(21) Appl. No.: 16/044,582

(22) Filed: Jul. 25, 2018

(65) Prior Publication Data
US 2018/0344811 A1   Dec. 6, 2018

Related U.S. Application Data

(63) Continuation of application No. 14/759,483, filed as application No. PCT/CN2014/070212 on Jan. 7, 2014, now abandoned.

(60) Provisional application No. 61/779,711, filed on Mar. 13, 2013, provisional application No. 61/749,570, filed on Jan. 7, 2013.

(51) Int. Cl.
| | |
|---|---|
| *A61K 38/21* | (2006.01) |
| *A61M 11/00* | (2006.01) |
| *A61K 9/00* | (2006.01) |
| *A61K 45/06* | (2006.01) |
| *A61K 31/5377* | (2006.01) |
| *A61K 31/7068* | (2006.01) |
| *A61K 33/24* | (2019.01) |
| *A61K 38/39* | (2006.01) |

(52) U.S. Cl.
CPC ............ *A61K 38/21* (2013.01); *A61K 9/0014* (2013.01); *A61K 9/0019* (2013.01); *A61K 9/0073* (2013.01); *A61K 31/5377* (2013.01); *A61K 31/7068* (2013.01); *A61K 33/24* (2013.01); *A61K 38/39* (2013.01); *A61K 45/06* (2013.01); *A61M 11/00* (2013.01)

(58) Field of Classification Search
None
See application file for complete search history.

(56) References Cited

U.S. PATENT DOCUMENTS

| | | | |
|---|---|---|---|
| 4,672,108 A | 6/1987 | Kung et al. | |
| 4,681,930 A | 7/1987 | Kung et al. | |
| 4,695,623 A | 9/1987 | Stabinsky | |
| 4,846,782 A | 7/1989 | Bonnem | |
| 4,897,471 A | 1/1990 | Stabinsky | |
| 5,372,808 A | 12/1994 | Blatt et al. | |
| 5,441,734 A | 8/1995 | Reichert et al. | |
| 5,480,640 A | 1/1996 | Morales et al. | |
| 5,573,781 A | 11/1996 | Brown et al. | |
| 5,602,232 A | 2/1997 | Reichert et al. | |
| 5,723,439 A | 3/1998 | Zhirnov et al. | |
| 5,874,304 A | 2/1999 | Zolotukhin et al. | |
| 5,972,331 A | 10/1999 | Reichert et al. | |
| 5,980,884 A | 11/1999 | Blatt et al. | |
| 6,087,478 A | 7/2000 | Vinkemeier et al. | |
| 6,579,695 B1 | 6/2003 | Lambalot et al. | |
| 6,670,127 B2 | 12/2003 | Evans | |
| 6,783,935 B2 | 8/2004 | Hijikata et al. | |
| 6,833,256 B1 | 12/2004 | Pontzer et al. | |
| 7,364,724 B2 | 4/2008 | Wei et al. | |
| 7,585,647 B2 | 9/2009 | Wei | |
| 10,441,636 B2 * | 10/2019 | Parker | A61P 35/04 |
| 2004/0202641 A1 | 10/2004 | Wei et al. | |
| 2005/0208019 A1 | 9/2005 | Wei | |
| 2006/0035327 A1 | 2/2006 | Wei | |
| 2008/0132681 A1 | 6/2008 | Hays | |
| 2009/0220456 A1 | 9/2009 | Wei | |

(Continued)

FOREIGN PATENT DOCUMENTS

| | | |
|---|---|---|
| AU | 2003248419 | 11/2003 |
| CN | 1062565 C | 2/2001 |

(Continued)

OTHER PUBLICATIONS

Kashima et al., American Journal of Roentgenology. 2010;194(2): 536-541 (Year: 2010).*

(Continued)

*Primary Examiner* — Gary B Nickol
*Assistant Examiner* — Jegatheesan Seharaseyon
(74) *Attorney, Agent, or Firm* — Law Office of Albert Wai-Kit Chan, PLLC

(57) ABSTRACT

The invention provides a method and/or composition for the treatment of bone cancer including primary bone cancer and secondary bone cancer, breast cancer, skin cancer, nasopharyngeal carcinoma, oral cancer, vulva cancer, prostate cancer, cervical cancer, melanoma including melanocarcinoma by percutaneous and/or transmucosal administration of the interferon. Further, the invention provides a method and/or composition for the treatment of skin, subcutaneous, mucosal and/or submucosal primary cancer and cancer metastatic lesions by percutaneous and/or transmucosal administration of the interferon, especially a method and/or composition for the treatment of bone cancer pain including pain resulted by secondary bone cancer.

20 Claims, No Drawings
Specification includes a Sequence Listing.

(56) References Cited

U.S. PATENT DOCUMENTS

| | | | |
|---|---|---|---|
| 2010/0261174 | A1 | 10/2010 | Grande et al. |
| 2012/0316322 | A1 | 12/2012 | Wei |
| 2013/0273527 | A1 | 10/2013 | Wei et al. |
| 2014/0341900 | A1 | 11/2014 | Harding et al. |
| 2016/0075771 | A1 | 3/2016 | Sidera et al. |

FOREIGN PATENT DOCUMENTS

| | | |
|---|---|---|
| CN | 1375502 | 10/2002 |
| EP | 0736303 | 1/1999 |
| WO | 9321229 A1 | 10/1993 |
| WO | 83/04053 | 1/1999 |
| WO | 93/21229 | 1/1999 |
| WO | 2002/036627 | 1/1999 |
| WO | 2002/086156 | 1/1999 |
| WO | 2005/034853 | 1/1999 |
| WO | 2005/067963 | 1/1999 |
| WO | 2006/134497 | 1/1999 |
| WO | 2014/106459 | 1/1999 |
| WO | 2015/070751 | 1/1999 |
| WO | 2001071007 A2 | 9/2001 |
| WO | 0280958 A1 | 10/2002 |
| WO | 2011084451 A2 | 7/2011 |

OTHER PUBLICATIONS

Gonzalez Vela et al., Journal of Clinical Oncology 23, No. 16_suppl (Jun. 1, 2005) 9078-9078. (Year: 2005).*

Lote et al. 1986, Acta Radiologica Oncology 25:4-6, p. 227-232 (Year: 1966).*

Avnet et al., Int. J.of Oncology, vol. 30: p. 469-467 (Year: 2007).*

Apr. 26, 2011 European Search Report for Huiyangtech (USA), Inc., Application No. EP 10 19 3126.9.

Jul. 28, 2009 European Office Action, Application No. EP 04809634. 1, Filed Mar. 26, 2006.

Sep. 20, 2007 Notification Concerning Transmittal of International Preliminary Report on Patentability (Chapter I of the Patent Cooperation Treaty) for PCT/IB2006/002340 for Guangwen Wei, Filed Mar. 9, 2006.

Jul. 23, 2002 International Search Report, Application No. PCT/CN02/00128 for Sichuan Biotechnology Research Center, "Recombination Super Compound Interferon Used as Hepatitis B Surface Antigen and E Antigen Inhibitor," Filed Feb. 28, 2002.

Mar. 28, 2011 Australian Office Action Guangwen Wei, Australian Application No. 2006257286, Filed Aug. 8, 2007.

Dec. 12, 2005 Australian Examiner's Report for Sichuan Biotechnology Research Center, Australian Application No. 2003248419, Filed Sep. 26, 2003.

Jun. 1, 2006 Australian Examiner's Report for Sichuan Biotechnology Research Center, Australian Application No. 2003248419, Filed Sep. 26, 2003.

Mar. 27, 2009 Chinese Office Action for 200480031910, Filed Apr. 28, 2006.

Aug. 30, 2006 Taiwanese Office Action for Sichuan Biotechnology Research Center, Taiwanese Application No. 92,123,846, Filed Aug. 28, 2003.

Dec. 12, 2008 Taiwan Examination Report for TW 95107930, filed Mar. 9, 2006.

Jan. 6, 2010 U.S. Office Action, U.S. Appl. No. 12/246,153.

Oct. 5, 2011 U.S. Office Action for U.S. Appl. No. 13/019,044, filed Feb. 1, 2011.

Feb. 23, 2012, Supplementary European Search report, European Application No. 06795349.7 Filed Oct. 4, 2007.

May 10, 2010 Indian Office Action, Indian Application No. 1214/MUMNP/2007.

Apr. 19, 2013 Korean Office Action, Korean Application No. 10-2012-7029545, Filed Nov. 12, 2012.

Jul. 16, 2014 PCT International search report and Written opinion for PCT/CN2014/000019, Filed Jan. 7, 2014.

Mar. 7, 2013 U.S. Office Action for U.S. Appl. No. 12/905,149, filed Oct. 15, 2010.

Sep. 10, 2014 U.S. Office Action, U.S. Appl. No. 13/861,617, filed Apr. 12, 2013.

Jun. 24, 2014 Korean Office Action for KR 10-2014-7010659, Filed Apr. 22, 2014.

Blatt, L.M. et al., 1996, "The biological activity and molecular characterization of a novel synthetic interferon-alpha species, consensus interferon," Journal of Interferon and Cytokine Research, 16(7)489-499.

Day, et al., "Engineered Disulfide Bond Greatly Increases Specific Activity of Recombinant Murine Interferon-Beta" Journal of Interferon Res. vol. 12, pp. 139-143 (1992).

Goldstein D. et al., 1998, "The role of interferon in cancer therapy: A current perspective", CA Cancer J Clin., 38:258-277.

Hu Xue-jun et al., 2006, "Meta-analysis of Maintenance Therapy With Interferon for Small Cell Lung Cancer", Chin J Evid-based Med, 6(11):809-814.

Jin Bo et al., 2006, "Meta-analysis of induction chemotherapy combined with interferon in Advanced Non-small Cell Lung Cancer", Chi J of Evidence-Based Medicine, pp. 370-375.

Klein, M.L. et al., 1998, "Structural characterization of recombinant consensus interferon-alpha," Journal of chromatography, 454:205-215.

Jin Bo, et al., 2007, "Meta-analysis of induction chemotherapy combined with interferon in small lung cancer", Chinese Journal of Practical Internal Medicine, 613-616.

Maffezzini M. et al., May 1996, "Salvage immunotherapy with subcutaneous recombinant interleukin 2 (rIL-2) and alpha-interferon (A-IFN) for stage D3 prostate carcinoma failing second-line hormonal treatment." Prostate, 28(5):282-6.

Melian EB et al., 2001, " Interferon alfacon-1: a review of its pharmacology and therapeutic efficacy in the treatment of chronic hepatitis C.", Drugs. 61(11):1661-91.

Moore, D.H. et al., "A phase I study of intraperitoneal interferon-alpha 2b and intravenous cis-platinum plus cyclophosphamide chemotherapy in patients with untreated state III epithelial ovarian cancer: a gynecologic oncology group pilot study," Gynecologic Oncology, 1995, 59:267-272.

Ozes, O.N. et al., 1992, "A comparison of interferon-con1 with natural recombinant interferons: antiviral, antiproliferative, and natural killer-inducing activities." J. Interferon Res., 12:55-59.

Pfeffer, L.M., 1997, "Biologic activity of natural and synthetic type 1 interferons," Seminars in Oncology, 24(3 suppl. 9):S9-63-S9-69.

Spada S., 2004, Directory of Approved Biopharmaceutic. Prod., 116-117.

Acosta-Rivero, Improvement of human interferon HUIFNα2 and HCV core protein expression levels in *Escherichia coli* but not of HUIFNα8 by using the tRNA AGA/AGG,BBRC,296(2002) 1303-1309.

Rang A. et al. "Effect of interferon alpha on hepatitis B virus replication and gene expression in transiently transfected human hepatoma cells", Nov. 1999, J Hepatol., 31(5):791-9.

Zheng, J. et al. "Effect of Recombinant Super-compound Interferon (rSIFN-co) on Human Breast Cancer Cells in vitro" J Sichuan Univ (Med Sci Edi), Feb. 28, 2010, vol. 41, No. 1, p. 29-34.

Chen, Y. et al. The Growth Inhibition and Apoptosis-promoting Effect of rSIFN-co to the Cervical Carcinoma Cells in vitro, Journal of Practical Obstetrics and Gynecology, Apr. 30, 2009, vol. 25, No. 4, p. 216-219.

Wu JB, et al., "Observation of efficacy of interferon treatment on giant cell tumor of limbs" Modern Journal of Integrated Traditional Chinese and Western Medicine. Dec. 31, 2008, 25(17), p. 3923-3924.

Larmonier N. et al., "An atypical caspase-independent death pathway for an immunogenic cancer cell line", Sep. 5, 2002, Oncogene, 21(39):6091-100.

te Poele RH et al., "DNA damage is able to induce senescence in tumor cells in vitro and in vivo", Mar. 15, 2002, Cancer Res., 62(6):1876-83.

Li HL, "The treatment of super interferon alpha on non-small cell lung cancer", Sep. 15, 2011, Chinese Master's Theses Full-text Database Medicine and Health Science, No. 9, p. 26-27.

(56) References Cited

OTHER PUBLICATIONS

Jun. 17, 2014 PCT International search report and Written opinion for PCT/CN2014/070212, Filed Jan. 7, 2014).
Whelan J et al., "The role of interferons in the treatment of osteosarcoma.", Pediatr Blood Cancer. Mar. 2010;54(3):350-4.
Nov. 20, 2017 Office Action, Japanese Application No. 2015-551113 for Superlab Far East Limited.
Yutaka Yata et al., 2010, A case of esophageal variceal bleeding induced by portal vein tumor thrombus of hepatocellular carcinoma, effectively treated with combined intra-arterial 5-fluorouracil and pegylated interferon-60 therapy, 565-571.
Jul. 12, 2018 Australian Office Action, Application No. 2014350714.
Jan. 10, 2019 Australian Office Action, Application No. 2014350714.
Jul. 18, 2018 Canadian Office Action, Application No. 2,784,624.
Aug. 20, 2018 Chinese Office Action, Application No. 2014800038986.
Sep. 17, 2018 Chinese Office Action, Application No. 2014800039353.
Aug. 14, 2018 Japanese Office Action, Application No. 2016-531672.
Aug. 20, 2018 Japanese Office Action, Application No. 2015-551117.
Jul. 10, 2018 Taiwanese Office Action, Application No. 1003100472.
Nov. 28, 2018 Taiwanese Office Action, Application No. 1003100470.
Dec. 3, 2018 European Extended Search Report, Application No. 167921857.
Wei et al., 2012, "Comparison of the Regulation of 13-Catenin Signaling by Type I, Type II and Type III Interferons in a Hepatocellular Carcinoma Cells", PlosOne, vol. 7, Issue 10.
Nakajima et al., 1988, "New basic biochemistry laboratory procedures 6, Measurement methods using biological activity", Japan, Apr. 30, 1988, p. 192-196.
Aug. 9, 2017 European Office Action, Application No. EP 14861341.
Oct. 18, 2017 Australian Office Action for Application No. 2014204386.
Oct. 18, 2017 Australian Office Action for Application No. 2014204368.
Dec. 21, 2017 Chinese Office Action for Chinese Application No. 201480003935.3.
Feb. 13, 2018 Korean Office Action for Korean Application No. 10-2012-7017945.
Mar. 22, 2018 Indian Office Action for Indian Application No. 6187/DELNP/2012.
Apr. 16, 2018 Korean Office Action for Korean Application No. 10-2012-7017945.
May 7, 2018 Taiwanese Office Action for TW 103100470.
Jun. 5, 2018 Australian Office Action for Application No. 2014204368.
Jul. 13, 2012 Korean Decision on Refusal of Patent.
May 16, 2019 European Office Action, Application No. EP 14735427.8.
Jun. 17, 2019 Japanese Office Action for Application No. 2015-551113.
Mar. 19, 2019 European Extended Search Report for Application No. 16792185.7.
May 7, 2019 Japanese Office Action for application # for 015-551113.
Schreiber G and Piehler J, "The molecular basis for functional plasticity in type I interferon signaling." Trends Immunol. Mar. 2015;36(3):139-49.
Chen Y et al. Study on the Susceptibility of the Cervical Carcinoma Cells to CTL Lysis under the Stimulation of rSIFN-co and Its Mechanism, Journal of Suchuan University, Medical Science Edition, Sep. 2008; 39(5): 715-718.
Argiriadi, Maria A. et al. Rational mutagenesis to support structure-based drug design: MAPKAP kinase 2 as a case study, BMC Structural Biology, Mar. 18, 2009.
Kashima et al., Radiofrequency ablation for the treatment of Bone metastasis from hepatocellular carcinoma, American Journal of Roentgenology. 2010;194(2): 536-541 (2010).
Mar. 29, 2019 Office Action for U.S. Appl. No. 16/038,704.
E. Kalie et al., An Interferon Mutant Optimized by Phage Display for IFNARI Binding Confers Specifically Enhanced Antitumor Activities 11, Journal of Biological Chemistry.
Booy, Stephanie et al., Influence of type-I Interferon receptor expression level on the response to type-I Interferons in human pancreatic cancer cells, Journal of Cellular and Molecular Medicine, vol. 18, No. 3, Jan. 25, 2014 (Jan. 25, 2014), pp. 492-502.
Bidwell et al. Silencing of Irf7 pathways in breast cancer cells promotes bone metastasis through immune escape. Nature Medicine. Aug. 2012;18(8):1224-31.
Slaney et al. The role of Type I interferons in immunoregulation of breast cancer metastasis to the bone. Oncoimmunology. Jan. 1, 2013; 2(1): e22339.
NCT00176527, Isotretinoin, Interferon Alfa-2b, Docetaxel, and Estramustine in Treating Patients With Metastatic Prostate Cancer That Did Not Respond to Hormone Therapy, Dec. 11, 2009 (Year: 2009).
"Virus Buster—Interferon" in Terminal Discovery—Superconductivity; Ed. Chengquang Di; Yanbian People's Publishing House, pp. 96-99, Jan. 2006.
Gebbia et al. Intracavitary Treatment of Malignant Pleural and Peritoneal Effusions in Cancer Patients. Anticancer Research 14: 739-746 (1994).
Zhang et al. In Vitro Inhibitory Effect of Gamma-interferon on Bone Resorption and Solid Tumor Metastasis. Med. J. Qilu. vol. 21, No. 1, pp. 26-28, Feb. 2006.
Wang et al. Gamma-interferon inhibits bone resorption and bone metastasis of lung cancer in vitro. Chinese Journal of Clinical Rehabilitation. vol. 9, No. 14, pp. 117-119, Apr. 14, 2005.
Schreiber et al. The molecular basis for functional plasticity in type I interferon signaling. Trends in Immunology. vol. 38, No. 3, pp. 139-149, Mar. 2015.
Ceballos et al. Interferon-alpha2b and transforming growth factor-beta1 treatments on HCC cell lines: Are Wnt/beta-catenin pathway and Smads signaling connected in hepatocellular carcinoma? Biochemical Pharmacology. vol. 82(11), pp. 1682-1691, Dec. 1, 2011.
Japanese Office Action, Jul. 2, 2019, for Superlab Far East Limited, Japanese Application No. 2016-531672.
Taiwanese Office Action, Jul. 26, 2019, for Superlab Far East Limited, Taiwanese Application No. 103100472, filed Jan. 6, 2014.
Japanese Office Action, Dec. 2, 2019, for Superlab Far East Limited, Japanese Application No. 2015-551117.
Taiwanese Office Action, Mar. 10, 2020, for Superiab Far East Limited, Taiwanese Application No. 103100472, filed Jan. 6, 2014.
Japanese Office Action, Mar. 31, 2020, for Superlab Far East Limited, Japanese Application No. 2016-531672.
Korean Office Action, May 8, 2020, for Superlab Far East Limited, Korean Application No. 10-2015-7021350.
Chinese Office Action, May 22, 2020, for Superlab Far East Limited, Chinese Application No. 2014800039353.
Taiwanese Office Action, Jun. 2, 2020, for Superlab Far East Limited, Taiwanese Application No. 108107884.
Japanese Office Action, Jun. 2, 2020, for Superlab Far East Limited, Japanese Application No. 2017-559434.
Canadian Office Office Action, Nov. 5, 2019, for Superlab Far East Limited, Canadian Application No. 2,897,335.
Canadian Office Action, Dec. 19, 2019, for Superlab Far East Limited, Canadian Application No. 2,897,312.
Indian Office Action, Jan. 31, 2020, for Superlab Far East Limited, Indian Application No. 201617019572.
Australian Office Action, Feb. 7, 2020, for Superlab Far East Limited, Austrialian Application No. 2016260845.
European Office Action, Mar. 2, 2020, for Superlab Far East Limited, European Application No. 14735273.6.
Japanese Office Action, dated Oct. 19, 2020, for Superlab Far East Limited, Japanese Application No. 2019-190263, filed Oct. 17, 2019.

\* cited by examiner

METHODS AND COMPOSITIONS FOR TREATMENT OF BONE, SKIN, SUBCUTANEOUS, MUCOSAL AND/OR SUBMUCOSAL CANCER BY PERCUTANEOUS AND/OR TRANSMUCOSAL ADMINISTRATION OF INTERFERON

CROSS-REFERENCE TO RELATED APPLICATIONS

This application is a continuation application of U.S. Ser. No. 14/759,483, filed Jul. 7, 2015, which is the National Stage of International Application No. PCT/CN2014/070212, filed Jan. 7, 2014, which claims benefit of U.S. Ser. No. 61/749,570, filed Jan. 7, 2013, and U.S. Ser. No. 61/779,711, filed Mar. 13, 2013. The entire contents and disclosures of the preceding applications are incorporated by reference into this application.

FIELD OF THE INVENTION

This invention relates to methods and products for treatment of cancer in subjects.

BACKGROUND OF THE INVENTION

Cancer, such as cancer in the bones, is a debilitating and painful disease and is often associated with metastases from primary tumors originating from other tissues or organs, but can also arise as primary tumors. As yet, there is no good, easily administered, effective treatment to alleviate the pain or treat the disease or give the people suffering from this disease any encouragement that their conditions could improve. Similarly, there is as yet no good, effective, easily administered treatment for skin cancer, subcutaneous cancer, mucosal and/or other submucosal cancers. Hence, there is an unmet medical need for the provision of methods, compositions and products for treatment of such diseases and the side effects of such diseases, such as bone pain.

SUMMARY OF THE INVENTION

The invention herein provides one or more methods and/or compositions and/or other products for the treatment of primary and/or secondary cancer in a subject, including for example cancer in the bone or bones (hereafter, "bone"), as well as skin cancer, subcutaneous cancer or carcinoma, mucosal cancer or carcinoma and/or other submucosal cancer or carcinoma, including metastasized lesions, and treatment of pain arising from the cancer, especially from bone cancer, in each instance, whether the cancer is primary or secondary, where secondary cancer refers to cancer from metastases originating from a primary tumor.

The invention provides a method and/or composition for the treatment of bone cancer including primary bone cancer and secondary bone cancer, breast cancer, skin cancer, nasopharyngeal carcinoma, oral cancer, vulva cancer, prostate cancer, cervical cancer, melanoma including melanocarcinoma by percutaneous and/or transmucosal administration of the interferon. Further, the invention provides a method and/or composition for the treatment of skin, subcutaneous, mucosal and/or submucosal primary cancer and cancer metastatic lesions by percutaneous and/or transmucosal administration of the interferon, especially a method and/or composition for the treatment of bone cancer pain including pain resulted by secondary bone cancer.

The invention provides one or more methods for the treatment of primary bone cancer or secondary bone cancer in a subject, comprising administering the interferon to an area of a bone of the subject where the bone is affected by cancer or comprises cancer cells.

The invention also provides one or more methods for the treatment of skin, subcutaneous, mucosal and/or submucosal cancer in a subject, comprising administering the interferon to a skin, subcutaneous, mucosal and/or submucosal area of the subject where the area is affected by cancer or comprises cancer cells, wherein such cancers are primary cancers or secondary cancers metastatic from primary cancers.

In some embodiments, the invention provides administering to the subject an effective amount of a consensus interferon alpha that comprises an amino acid sequence of SEQ ID NO: 1 and having anti-cancer activity. In some embodiments, the amino acid sequence is encoded by a polynucleotide comprising a polynucleotide sequence of SEQ ID NO:2

In some embodiments of the invention, the interferon is administered by local administration, such as to an area affected by cancer or comprising cancer cells.

In some embodiments of the invention, the interferon is administered by local administration and at least one of inhalation administration and systemic administration.

In some embodiments, the invention provides methods and compositions for treating bone cancer (including primary bone cancer and secondary bone cancer), breast cancer, skin cancer, nasopharyngeal carcinoma, oral cancer, carcinoma of the vulva, prostatic carcinoma, cervical carcinoma and melanoma (including melanocarcinoma) by percutaneous and/or transmucosal administration.

In some embodiments, the invention provides methods and compositions for treating primary skin cancer, subcutaneous carcinoma, mucosal carcinoma and/or submucosal carcinoma as well as metastasized lesions, including methods and compositions for treating pain caused by bone cancer (including secondary bone cancer).

In some embodiments, the invention provides methods and compositions as any described herein, where the interferon is administered by local administration, inhalation administration, or systemic administration, where systemic administration includes subcutaneous administration and intramuscular administration, such as subcutaneous injection and intramuscular injection.

In some embodiments, the invention provides methods and compositions as any described herein, further comprising administering the interferon by at least one of injection and inhalation of aerosolized interferon.

In some embodiments, the invention provides methods and compositions for treating cancer as any described herein, where the interferon is administered by local administration, or optionally by percutaneous administration and/or transmucosal administration.

The skin cancer herein includes cancer involving the epidermal cells such as basal cell carcinoma, epidermoid carcinoma, squamous cell carcinoma, including melanoma (including melanocarcinoma) cervical carcinoma, and carcinoma of the vulva. The subcutaneous cancer herein involves cancer of the subcutaneous tissues or cells and includes breast and prostatic cancer or carcinoma and the like. The mucosal cancer herein involves cancer of the mucosal cells and includes nasopharyngeal carcinoma, oral cancer, and rectal carcinoma. The submucosal tumor includes cancer of the submucosal tissues including bone cancer.

In some embodiments, the invention provides methods, compositions and/or other products for treating bone cancer, skin cancer, subcutaneous cancer, mucosal cancer and/or submucosal cancer and/or cancer pain by local administration of the interferon, and local administration includes percutaneous administration and/or transmucosal administration.

The invention provides, in some embodiments, administering the interferon to an area of a bone of the subject where the bone is affected by cancer or comprises cancer cells. The cancer in the bone can be primary bone cancer or can be secondary bone cancer, that is, a cancer that has metastasized to the bone from a primary tumor that originates from another tissue or organ.

The invention also provides methods and compositions for treatment of cancer in a subject comprising administering to the subject an effective amount of a consensus interferon alpha that comprises anti-cancer activity and an amino acid sequence of SEQ ID NO: 1, wherein the interferon is administered by local administration to the skin and/or to the mucosa of the subject.

The invention additionally provides a method as any of the foregoing methods, where the interferon is administered by percutaneous administration or systemic administration.

In some embodiments, systemic administration includes subcutaneous administration and intramuscular administration.

The invention moreover provides a method as any of the foregoing methods, further providing administering the interferon to the subject systemically by injection, such as subcutaneous injection and intramuscular injection.

The invention additionally provides a method as any of the foregoing methods, further comprising administering the interferon to the subject by inhalation. In some embodiments, inhalation administration includes administration of a dried interferon powder. In some embodiments, inhalation administration includes administration of an aqueous solution of the interferon. In some embodiments, inhalation administration includes administration of an aerosolized form of the interferon.

The invention also provides a method of treatment of cancer in bone in a subject comprising administering to the subject an effective amount of a consensus interferon alpha that comprises anti-cancer activity and an amino acid sequence of SEQ ID NO: 1, wherein the interferon is administered percutaneously to the subject.

The invention additionally provides a method as the foregoing method of application of the interferon percutaneously, on or to the skin of the subject, and/or transmucosally, to or on the mucosa of the subject.

The invention further provides a method percutaneously and/or transmucosally as the foregoing, further comprising administering the interferon by at least one of: injection and inhalation, optionally, by both injection and inhalation administration, where the inhalation administration includes administration of an aerosolized form of the interferon, a dry powder and/or an aqueous solution of the interferon.

The invention further provides a method as any of the foregoing methods, wherein application of interferon to an area of the bone includes at least one of: application of the interferon directly or indirectly to or on the bone.

The invention also provides a method as any of the foregoing methods, wherein application of interferon to the skin comprises application to or on the skin in proximity to the bone affected by cancer, that is, that part of the bone that comprises cancer cells or application to or on the skin surrounding the bone affected by cancer.

In some embodiments, the administration to the skin includes application of the interferon to the skin surrounding the bone affected by cancer.

The invention further provides a method as any of the foregoing methods, where the interferon is administered to the mucosa. In some embodiments, application to the mucosa includes application to the mucosa in proximity to the bone affected by cancer, that is, that part of the bone comprising cancer cells, or to the mucosa surrounding the bone affected by cancer.

The invention also provides a method as any of the foregoing methods, wherein application of the interferon to the skin includes application of the interferon subcutaneously.

The invention further provides a method as any of the foregoing methods, wherein application of the interferon to the mucosa includes submucosal administration.

The invention moreover provides a method as any of the foregoing methods, wherein application of the interferon to the skin comprises at least one of: spraying an aqueous solution of the interferon on skin, applying a cream comprising the interferon on skin, applying a membrane, such as a transdermal patch comprising the interferon, or any other membrane comprising the interferon that allows for controlled-release or permeation or diffusion of the interferon to and through skin of subject, or creating a depot effect such that interferon is deposited under the skin and produces a slow-release or controlled release effect, and/or other closed drug delivery systems.

The invention further provides a method as any of the foregoing methods, wherein administering the interferon by inhalation comprises at least one of: delivering the interferon intranasally and to the lungs.

The invention also provides a method as any of the foregoing methods, wherein the interferon is formulated as a solution or a suspension.

The invention provides a method as any of the foregoing methods wherein the interferon is formulated in the form of at least one of: nanoparticles, microspheres, liposomes or other controlled release single or composite material.

The invention also provides a method as any of the foregoing methods, wherein the interferon administered by injection is administered in at least two or more dosages, each dosage being higher than or the same as the previous dose.

The invention provides a method as any of the foregoing methods, wherein the first dose of injection of the interferon comprises about 2 microgram to about 15 microgram of the interferon.

The invention provides a method as any of the foregoing methods, wherein the first dose of injection of the interferon comprises 9 microgram or 15 microgram of interferon.

The invention also provides a method as any of the foregoing methods, where the second dose of injection of the interferon comprises about 15 microgram to about 50 microgram of the interferon.

The invention also provides a method of any of the foregoing embodiments, wherein the second dose of injection of the interferon comprises 15 microgram or 18 microgram or 21 microgram of the interferon.

The invention provides a method as any of the foregoing methods, wherein the third dose and/or any subsequent dose of injection of the interferon is higher or the same as the second dose.

The invention further provides a method as any of the foregoing methods, wherein administering the interferon by application to the skin or the bone or the mucosa comprises spraying thereon at least 1-12 times a day, optionally 2-10 times a day, still optionally, 3-8 times a day, further optionally 4 or 5 or 6 times per day.

The invention still further provides a method as any of the foregoing methods, wherein administering the interferon to the subject by inhalation comprises administering the interferon by inhalation every day or every few days, such as every 2 days or every 3 days.

The invention provides a method as any of the foregoing methods, wherein administering the interferon to the subject to or on the bone or skin or mucosa or other local administration comprises applying a formulation of the interferon at a concentration in the range of about 0.01 mg/ml to about 5 mg/ml optionally, in the range of about 0.03 mg/ml to about 2 mg/ml and further optionally, in the range of about 0.05 mg/ml to about 1 mg/ml, and still further optionally, in the range of about 0.1 mg/ml to about 0.5 mg/ml.

The invention provides a method as any of the foregoing methods, wherein the primary tumor comprises at least one of: a solid tumor and a non-solid tumor.

Further, the invention provides that the primary tumor that metastasized can be cancer of the respiratory system, cancer of the digestive system, cancer of the urinary system, breast cancer, skin cancer, cancer of the reproductive system, head and neck cancer, cancer of the hormonal system, and cancer of the nervous system. The cancer of the digestive system includes: oral cancer, tongue cancer, laryngeal carcinoma, esophageal cancer, gall bladder cancer, liver cancer, gastrointestinal cancer, and pancreatic cancer. The cancer of the reproductive system includes: carcinoma of the external genitalia, cervical cancer, endometrial cancer, uterine cancer, ovarian cancer, and prostate cancer. The cancer of the respiratory system includes: lung cancer and nasopharyngeal carcinoma. The cancer of the urinary system includes: kidney cancer and bladder cancer. The cancer of the hormonal system includes: adrenal cancer and thyroid cancer. The head and neck cancer comprises nasopharyngeal carcinoma. The skin cancer includes: epithelial and subcutaneous cancer such as prostatic carcinoma, breast cancer, basal cell carcinoma, epidermoid carcinoma, squamous cell carcinoma, carcinoma of the external genitalia such as carcinoma of the vulva, and melanoma including melanocarcinoma. The cancer of the nervous system includes: neuroma, malignant neuroma, glioma, and astrocytoma.

The invention provides that the lung cancer includes: small cell lung cancer and non-small cell lung cancer. The gastrointestinal cancer includes: gastrointestinal interstitial cell tumor, stomach cancer, colon cancer, rectal cancer, and colorectal cancer. The gall bladder cancer includes cholangiocarcinoma. The liver cancer includes hepatocellular carcinoma. The kidney cancer includes renal cell carcinoma. The bladder cancer includes superficial bladder cancer.

The invention further provides that the primary tumor that metastasized can be: a carcinoma, a sarcoma, and a rhabdomyosarcoma.

The invention further provides that the primary tumor that metastasized can also be one of: abdominal tumor, myoepithelial carcinoma, synovial sarcoma, hemangioma, lymphoma and Kaposi's sarcoma.

The invention also provides that the mucosal cancer includes oral cancer, nasopharyngeal carcinoma, rectal cancer, laryngeal carcinoma and tongue cancer.

The invention provides a method as any of the foregoing methods, where the bone cancer, skin cancer, subcutaneous carcinoma, mucosal carcinoma and/or submucosal carcinoma includes bone cancer (including primary bone cancer and secondary bone cancer), breast cancer, skin cancer, nasopharyngeal carcinoma, oral cancer, carcinoma of the vulva, prostatic carcinoma, cervical carcinoma and melanoma, including melanocarcinoma.

The invention provides a method as any of the foregoing methods, wherein injection of the interferon comprises injection before, after, or at about the same time as the administration of the interferon to or on the skin and/or bone, and/or mucosa, and/or submucosa.

The invention further provides a method as any of the foregoing methods, wherein application of the interferon by inhalation comprises such application before, after or approximately at the same time as application of the interferon to or on the skin and/or bone, and/or mucosa, and/or submucosa.

The invention provides a method as any of the foregoing methods, wherein administration of the interferon to or on the skin, bone, mucosa, and/or submucosa comprises such administration before, after, or at the same time as administration of the interferon by injection and/or administration of the interferon by inhalation, and the administration of the interferon by injection comprises such administration before, after, or at about the same time as administration of the interferon by inhalation, if any.

The invention provides that for local administration, the interferon can be applied to or on the cancerous lesion. Further, application to or on the cancerous lesion can be by: at least one of infiltration administration, percutaneous administration, transdermal administration, epidermal administration, and transmucosal administration. Percutaneous administration can also be achieved by spraying the interferon.

The invention also provides that local administration of the interferon comprises administration of interferon in a range of about 2 microgram to about 2100 microgram, optionally, in a range of about 4 microgram to about 1800 microgram, further optionally, in a range of about 9 microgram to about 1500 microgram, still optionally, in a range of about 12 microgram to about 1200 microgram, still further optionally, in a range of about 15 microgram to about 1000 microgram, yet further optionally, in a range of about 18 microgram to about 900 microgram, still yet optionally, in a range of about 21 microgram to about 750 microgram, and still further optionally, in a range of about 24 microgram to about 600 microgram.

The invention provides that when the interferon is administered locally to the subject, it can be administered in a range of about 1-12 times per day, optionally, 2-10 times per day, still optionally, 3-8 times per day, and still further optionally, 4-6 times per day.

In some embodiments, the invention provides that when the interferon is administered to the subject locally, it can be administered at least 1, 2, 3, 4, 5, 6, 7, 8, or more times per day.

The invention additionally provides that when the interferon is administered to the subject by local administration, the interferon can be administered every day, or every other day, or every $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, or $21^{st}$ day, or every month, or every 2, or 3, or 4, or 5, or 6 or 7, or 8, or 9, or 10, or 11, or 12 months or longer.

The invention moreover provides a method as of the foregoing, where administration of the interferon can be by spraying, and the spray can be in an amount in a range of about 6 microgram to about 100 microgram, optionally, in a range of about 10 microgram to about 80 microgram, further optionally, in a range of about 20 microgram to about 60 microgram, and still further optionally, in a range of about 30 microgram to about 40 microgram per spray administration and at a concentration in a range of about 0.01 mg/ml to about 5 mg/ml, optionally, about 0.03 mg/ml to about 2 mg/ml, further optionally, about 0.05 mg/ml to about 1 mg/ml, and still optionally, about 0.1 to 0.5 mg/ml.

The invention further provides a method as any of the foregoing, where the interferon can be administered by spraying 1-10 times per day, optionally, 2-9 times per day, further optionally, 3-8 times per day, still optionally 4-7 times per day, yet still optionally 5-6 times per day.

The invention also provides a method as any of the foregoing, where the interferon for local administration can be formulated as at least one of: an aqueous solution, such as for spraying, a membrane permeation or diffusion drug delivery system, a controlled release drug delivery system, a closed drug delivery system, a patch such as a transdermal patch, or a depot comprising the interferon injected under the skin, producing a slow-release effect.

The invention also provides a method as any of the foregoing, where the interferon administered by systemic administration is administered before, at about the same time, and/or after the percutaneous administration of the interferon. The systemic administration includes subcutaneous administration and intramuscular administration. Optionally, the systemic administration includes subcutaneous injection and intramuscular injection.

The invention further provides a method as any of the foregoing, where the interferon when administered by systemic administration, can be administered in an amount in a range of about 2 microgram to about 70 microgram, optionally in a range of about 4 microgram to about 50 microgram, further optionally, in a range of about 9 microgram to about 30 microgram, still optionally, in a range of about 15 microgram to about 24 microgram, still further optionally, in a range of about 18 microgram to about 21 microgram, per injection.

The invention moreover provides a method as any of the foregoing, when the interferon is administered by systemic administration, it is administered at least once every 1-8 days, optionally, at least once every 2-7 days, still optionally, at least once every 3-6 days, further optionally, at least once every 4-5 days. Still optionally, the interferon can be administered every 1-2 days.

The invention further provides a method as any of the foregoing, where the duration of the systemic interferon administration is at least for 1 day, 2 days, 3 days, 4 days, 5 days, 6 days, 7 days, 8 days, 9 days, 10 days, 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, 3 years, 4 years, 5 years, and 6 years.

The invention also provides a method as any of the foregoing methods, wherein the duration of the interferon administration is for a period of time in a range of 1 day to 6 years, optionally, 1 week to 4 years, still optionally, 2 weeks to 3 years, further optionally, 1 month to 1 year, still further optionally, 2 months to 9 months, or longer, or throughout the remaining life of the subject.

The invention also provides a method as any of foregoing methods, wherein the interferon is administered by subcutaneous or intramuscular injection at least 2 times, optionally, at least 4 times, further optionally, at least 6 times, still optionally, at least 8 times, still further optionally, at least 10 times.

The invention further provides a method as any of the foregoing systemic administration or injection methods, wherein the interferon is administered in at least one initial induction dose in a range of about 2 microgram to about 15 microgram, optionally, about 3 microgram to about 10 microgram, still optionally about 4.5 microgram to about 9.5 microgram, further optionally, about 4 microgram to about 9 microgram, and still further optionally, at about 4.5 microgram or 9 microgram.

The invention also provides a method of any of the foregoing systemic administration or injection methods, wherein, the interferon is further administered in at least one subsequent therapeutic dose in a range of about 10 microgram to about 70 microgram each time, optionally in a range of about 12 microgram to about 50 microgram each time, further optionally in a range of about 15 microgram to about 30 microgram each time.

The invention additionally provides a method of any of the foregoing systemic administration or injection methods, wherein the time interval between the induction dose and the therapeutic dose of the interferon is in a range of about 1 day to about 1 month, optionally or preferably, in a range of about 1 days to about 3 week, including a range of about 1 day to about 3 days, or is 1, day, 2 days, 3 days, 4 days, 5 days, 6 days, 7 days, 8 days, 9 days, 10 days, 1 week, 2 weeks and 3 weeks.

The invention also provides a method as any of the foregoing systemic administration or injection methods, wherein the interferon is administered to the subject at a frequency of about once every day or about once every 2, 3, 4, 5, 6, 7, 8, 9, or 10 days, optionally, in a range of about once every 1-7 days, further optionally, about once every 1-2 days, at the induction dose.

The invention further provides a method as any of the foregoing systemic administration or injection methods, wherein the interferon is administered to the subject at a frequency of about once every day or about once every 2, 3, 4, 5, 6, 7, 8, 9, or 10 days, optionally, in a range of about once every 1-7 days, further optionally, about once every 1-2 days, at the therapeutic dose.

The invention also provides a method as any of the foregoing systemic administration or injection methods, wherein the duration of administration of the induction dose and the therapeutic dose is at least: 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, or 6 years, or optionally over the remaining life of the subject.

The invention moreover provides a method as any of the foregoing inhalation administration methods, wherein the inhalation administration comprises at least one of: pulmonary inhalation and nasal inhalation.

The invention further provides a method as any of the foregoing inhalation administration methods, wherein the interferon for inhalation administration comprises at least one of: dry powder and aerosolized interferon.

The invention also provides a method as any of the foregoing inhalation administration methods, wherein the interferon is administered in an amount in a range of about 100 microgram to about 2000 microgram, optionally, about 120 microgram to about 1500 microgram, further optionally, about 150 microgram to about 1200 microgram, still optionally, about 200 microgram to about 900 microgram, yet further optionally, about 450 microgram to about 750 microgram, still further optionally, about 500 microgram to about 650 microgram, still yet further optionally, at 600 microgram, by one inhalation administration.

The invention also provides a method as any of the foregoing inhalation administration methods, wherein the interferon is administered by inhalation administration about once every 1 or 2 or 3 days, optionally, every day.

The invention also provides a method as any of the foregoing inhalation administration methods, wherein the duration of inhalation administration is in a range of about 1 day to about 6 years, optionally, about 1 week to about 4 years, further optionally, about 2 weeks to about 3 years, still optionally, about 3 weeks to about 2 years, still further optionally, about 1 month to about 1 year, or yet further optionally, about 2 months to about 9 months.

The invention also provides a method as any of the foregoing inhalation administration methods, wherein the duration of inhalation administration is at least 1 day, 2 days, 3 days, 4 days, 5 days, 6 days, 7 days, 8 days, 9 days, 10 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, or 6 years, or optionally for a long time, such as over the remaining life of the subject.

The invention additionally provides a method as any of the foregoing methods, wherein the interferon is administered as a monotherapy.

The invention also provides a method as any the foregoing methods, further including administering to the subject at least one other anti-cancer therapy.

The invention also provides a method as any of the foregoing methods, wherein the at least one other anti-cancer therapy is administered to the subject before, simultaneously or at about the same time, and/or after administration of the interferon.

The invention also provides a method as any of the foregoing methods, wherein the at least one other anti-cancer therapy comprises at least one of: chemotherapy, radiotherapy, surgical therapy, interventional therapy, biotherapy, targeted therapy, and Traditional Chinese medicine.

The invention further provides a method as any of the foregoing methods, wherein the biotherapy comprises at least one of gene therapy and immunotherapy, and the surgical therapy comprises ablation therapy.

The invention also provides a method as any of the foregoing methods, wherein the treatment achieves at least one of: elimination of at least one cancer lesion, reduction in size of at least one cancer lesion, and non-progression of growth of at least one cancer lesion, as compared to before treatment.

The invention further provides a method as any of the foregoing methods, wherein the at least one anti-cancer therapy is a non-surgical therapy.

The invention additionally provides a sprayer for administering an interferon that comprises anti-cancer activity and an amino acid sequence of SEQ ID NO: 1, wherein the interferon is formulated in an amount for administering at least 1-12 times, optionally, 2-10 times, further optionally, 3-8 times, still optionally, 4 or 5 or 6 times.

The invention provides a sprayer as the foregoing sprayer, wherein the amount of interferon comprises a concentration in a range of at least about 0.01 mg/ml to about 5 mg/ml, optionally, about 0.03 mg/ml to about 2 mg/ml, still optionally, about 0.05 mg/ml to about 1 mg/ml, further optionally, about 0.1 mg/ml to about 0.5 mg/ml.

In some embodiments, the amount of interferon in any of the foregoing sprayer can include about 0.1 mg/ml, about 0.2 mg/ml, about 0.3 mg/ml, about 0.4 mg/ml or about 0.5 mg/ml of the interferon.

The invention also provides a sprayer as any of the foregoing sprayer, wherein the sprayer is a single use sprayer comprising one day's supply of the interferon.

The invention further provides a sprayer as any of the foregoing sprayer, wherein the sprayer is a multiple use sprayer comprising at least a one-week supply of the interferon.

The invention provides a sprayer for administration of a consensus interferon alpha to a subject, wherein the interferon comprises anti-cancer activity and an amino acid sequence of SEQ ID NO: 1, and is formulated at a concentration of 300 microgram/ml.

The invention additionally provides a sprayer as forementioned, wherein the interferon is formulated in an aqueous solution in a volume of 2 ml.

The invention also provides a sprayer as any of the foregoing sprayer, wherein the interferon is encoded by a polynucleotide comprising the sequence of SEQ ID NO:2.

The invention moreover provides a measured or metered dose of an interferon comprising a single use amount of the interferon, wherein the interferon comprises anti-cancer activity and an amino acid sequence of SEQ ID NO: 1.

The invention also provides a metered dose as the foregoing metered dose, wherein the metered dose comprises the interferon in an amount in a range of about 100 microgram to about 2000 microgram, optionally, about 120 microgram to about 1500 microgram, further optionally or preferably, about 150 microgram to about 1200 microgram, still optionally or more preferably, about 200 microgram to about 900 microgram, yet optionally or further preferably, about 450 microgram to about 750 microgram, still further optionally or still more preferably, about 500 microgram to about 650 microgram, and yet optionally or preferably, 600 microgram of the interferon.

The invention provides a metered dose as any of the foregoing metered dose, further comprising an additional amount of the interferon, sufficient for at least one week of treatment.

The invention provides a metered dose as any of the foregoing metered dose, wherein the metered dose is formulated for inhalation.

The invention provides a metered dose for inhalation as above, wherein the metered dose is formulated for inhalation via the nose or for inhalation via the lungs.

The invention provides a metered dose as any of the foregoing metered dose, wherein the interferon was aerosolized.

The invention moreover provides a transdermal patch comprising an interferon, wherein the interferon comprises anti-cancer activity and an amino acid sequence of SEQ ID NO: 1, and wherein the patch allows diffusion or permeation of the interferon to the skin of a subject.

The invention also provides a sprayer as any of the foregoing sprayers, wherein the sprayer comprises at least a two-week supply of the interferon.

The invention also provides a sprayer as any of the foregoing sprayers, wherein the sprayer is configured and formulated for delivery of the interferon to the nose.

The invention also provides a sprayer as any of the foregoing sprayers, wherein the sprayer is configured and formulated for delivery of the interferon to or on at least one of: the subject's skin or bone or mucosa.

The invention additionally provides a sprayer as any of the foregoing sprayers, wherein the sprayer is configured and formulated for delivery of the interferon by inhalation for delivery to the lungs of the subject, such as an inhaler.

The invention also provides a metered dose of a consensus interferon alpha that comprises anti-cancer activity for inhalation, wherein the metered dose comprises interferon in an amount in the range of about 100 microgram to about 2000 microgram, optionally, about 200 microgram to about 1000 microgram, still optionally about 300 microgram to about 900 microgram, further optionally, about 400 microgram to about 800 microgram, still further optionally, about 500 microgram to about 700 microgram, yet further optionally, about 600 microgram.

The invention provides a metered dose as any of the foregoing embodiments, wherein the metered dose is formulated for intranasal application.

The invention moreover provides a method of preparation of a medicament, wherein the medicament comprises consensus interferon alpha that comprises anti-cancer activity for administration to a subject who has cancer in bone, wherein the interferon is formulated in at least two distinct formulations, one for injection and one for percutaneous application to or on the skin or bone of the subject.

The invention also provides a method of preparation of a medicament as of the foregoing embodiment, wherein the interferon is further formulated in a third formulation, for inhalation administration.

The invention further provides use of a consensus interferon alpha having an amino acid sequence of SEQ ID NO: 1 and anti-cancer activity in the preparation of medicaments for treatment of bone cancer, skin cancer, subcutaneous carcinoma, mucosal carcinoma and/or submucosal carcinoma in subjects.

The invention additionally provides use of a consensus interferon alpha having an amino acid sequence of SEQ ID NO: 1 and anti-cancer activity in the preparation of medicaments for treatment of pain associated with cancer, including bone cancer, in subjects.

The invention also provides a drug composition for treatment of bone cancer, skin cancer, subcutaneous carcinoma, mucosal carcinoma and/or submucosal carcinoma in subjects, where the composition contains a consensus interferon alpha having an amino acid sequence of SEQ ID NO:1 and anti-cancer activity.

The invention further provides a drug for treatment of pain associated with cancer, such as bone cancer, in subjects. This composition contains a consensus interferon alpha that has an amino acid sequence of SEQ ID NO: 1 and anti-cancer activity.

DETAILED DESCRIPTION OF THE INVENTION

The terms used in this application are intended to have their ordinary meaning as understood by persons skilled in the art, unless specifically indicated otherwise. In addition, the following terms have the additional meanings, as specified herein.

The term "anti-cancer activity" as used herein includes any activity that arrests or suspends the growth of cancer cells or the progression of the disease, including causing apoptosis or necrosis of cancer cells, stopping the progression of their growth or cell cycle, or inducing tumor shrinkage or disappearance of tumor.

The term "biotherapy" as used herein includes any and all biologics that are or can be used for treatment of cancer or side effects of cancer treatment and includes but is not limited to: antibodies, recombinant proteins, microRNA, siRNA, gene therapy, viral therapy, and cell therapy. Endostar and antibodies such as Rituxin, Herceptin, Avastin are examples drugs having anti-cancer effects that can be used herein. NK cell therapy is an example of cell therapy that can be used herein.

The term "bone pain" or "pain associated with cancer" as used herein includes sensation of pain recognized by a subject as being related to cancer, including cancer in the bone.

The term "cancer" as used herein includes primary cancer as well as secondary cancer that metastasized from a primary tumor arising from another tissue or organ.

The term "cancer-affected bone" as used herein means a bone or an area of the bone that contains cancer cells.

The term "cancer in bone" as used herein means the presence of cancer cells in one or more bones in reference to a subject. Such cancer cells may arise from a primary bone cancer or secondary bone cancer, that is, cancer that have metastasized from a primary tumor, such as originating from another tissue or organ in the body.

The term "comprises" or "comprising" as used herein means has/have or having, contains or containing, includes or including, and/or is or being, and is not to be interpreted as limiting to the specified element or elements, but may encompass unspecified element or elements.

The term "consensus interferon alpha" as used herein means a polypeptide having the amino acid sequence of the interferon as described in U.S. Pat. Nos. 7,364,724, 7,585,647, 8,114,395 and 8,287,852. The amino acid sequence is shown as SEQ ID NO:1. The amino acid sequence can be encoded by a polynucleotide having the sequence of SEQ ID NO:2. In one aspect, the amino acid sequence of the interferon, such as that made by recombinant techniques, as well as the nucleotide sequence encoding the same (together with a termination codon), are shown below as SEQ ID NO:1 and SEQ ID NO:2, respectively. These sequences are also referenced in U.S. Pat. Nos. 7,585,647; 7,364,724; 8,114,395 and 8,287,852:

```
    M   C   D   L   P   Q   T   H   S   L   G   N   R   R   A   L   I   L   L   A
  1 ATGTGCGACC TGCCGCAGAC CCACTCCCTG GGTAACCGTC GTGCTCTGAT CCTGCTGGCT
    TACACGCTGG ACGGCGTCTG GGTGAGGGAC CCATTGGCAG CACGAGACTA GGACGACCGA

Q   M   R   R   I   S   P   F   S   C   L   K   D   R   H   D   F   G   F   P
 61 CAGATGCGTC GTATCTCCCC GTTCTCCTGC CTGAAAGACC GTCACGACTT CGGTTTCCCG
    GTCTACGCAG CATAGAGGGG CAAGAGGACG GACTTTCTGG CAGTGCTGAA GCCAAAGGGC

Q   E   E   F   D   G   N   Q   F   Q   K   A   Q   A   I   S   V   L   H   E
121 CAGGAAGAAT TCGACGGTAA CCAGTTCCAG AAAGCTCAGG CTATCTCCGT TCTGCACGAA
    GTCCTTCTTA AGCTGCCATT GGTCAAGGTC TTTCGAGTCC GATAGAGGCA AGACGTGCTT

M   I   Q   Q   T   F   N   L   F   S   T   K   D   S   S   A   A   W   D   E
181 ATGATCCAGC AGACCTTCAA CCTGTTCTCC ACCAAAGACT CCTCCGCTGC TTGGGACGAA
    TACTAGGTCG TCTGGAAGTT GGACAAGAGG TGGTTTCTGA GGAGGCGACG AACCCTGCTT
```

```
                 -continued
         S   L   L   E   K   F   Y   T   E   L   Y   Q   Q   L   N   D   L   E   A   C
241      TCCCTGCTGG AAAAATTCTA CACCGAACTG TACCAGCAGC TGAACGACCT GGAAGCTTGC
         AGGGACGACC TTTTTAAGAT GTGGCTTGAC ATGGTCGTCG ACTTGCTGGA CCTTCGAACG V   I   Q   E   V   G   V   E   E   T   P   L   M   N   V   D   S   I   L   A
301      GTTATCCAGG AAGTTGGTGT TGAAGAAACC CCGCTGATGA ACGTTGACTC CATCCTGGCT
         CAATAGGTCC TTCAACCACA ACTTCTTTGG GGCGACTACT TGCAACTGAG GTAGGACCGA V   K   K   Y   F   Q   R   I   T   L   Y   L   T   E   K   K   Y   S   P   C
361      GTTAAAAAAT ACTTCCAGCG TATCACCCTG TACCTGACCG AAAAAAAATA CTCCCCGTGC
         CAATTTTTTA TGAAGGTCGC ATAGTGGGAC ATGGACTGGC TTTTTTTTAT GAGGGGCACG A   W   E   V   V   R   A   E   I   M   R   S   F   S   L   S   T   N   L   Q
421      GCTTGGGAAG TTGTTCGTGC TGAAATCATG CGTTCCTTCT CCCTGTCCAC CAACCTGCAG
         CGAACCCTTC AACAAGCACG ACTTTAGTAC GCAAGGAAGA GGGACAGGTG GTTGGACGTC E   R   L   R   R   K       E   (SEQ ID NO: 1)
481      GAACGTCTGC GTCGTAAAGA ATAA   (SEQ ID NO: 2)
         CTTGCAGACG CAGCATTTCT TATT   (SEQ ID NO: 3)
```

The term "effective amount" as used herein means an amount that can produce a desired, beneficial or therapeutic effect.

The term "in proximity to the bone" as used herein means in close contact with the bone, including but not limited to the skin covering protrusions such as the clavicle, the ribs, the joints, etc., or the mucosa surrounding a bone, such as a bone affected by cancer.

The term "inhalation" as used herein includes inhalation by breathing in through the nose, such as by intranasal administration, or breathing in through the lungs, such as via the throat or nasopharynx by pulmonary administration.

The term "injection" as used herein means delivery of a substance such as a drug, for example, the interferon herein, by puncturing the skin, and includes injection into one or more of a tissue or organ or a body cavity, such as injection into the muscle (intramuscular injection), the peritoneal cavity (intraperitoneal injection), a blood vessel (intravenous injection), a tumor (intratumoral injection), under the skin (subcutaneous injection), or into a lymph node, or the thoracic cavity, and the like.

The term "local administration" in reference to the interferon as used herein means administering or applying the interferon to a specified area of the body. Local administration can be administration to an area of a tissue, such as the skin, the bone, the nasal cavity, the throat or nasopharynx, the lungs (as when exposed during surgery), or to an area of an organ (as when exposed during surgery). Local administration may be topical or percutaneous, such as applying to or on the surface of the skin, or transmucosal, such applying to or on the surface of the mucosa, such as the oral cavity. Local administration can include the deposition of a drug depot for slow- or controlled release under the skin.

The term "pharmaceutically acceptable carrier or excipients" means any and all dry or aqueous ingredients that are conventionally approved by regulatory authorities for use to formulate medicines for administration to human subjects. Each such carrier or excipient may, by itself, not have any therapeutic value, but may also be used as an adjunct, enhancing the therapeutic value of the interferon to be administered.

The term "sprayer" as used herein means a device for delivery of a drug by spraying, such as by spraying the interferon, into the nose or throat of the subject for inhalation administration or by spraying the drug onto the skin or bone or mucosa of the subject for local, percutaneous or transmucosal administration. The sprayer herein can deliver an aqueous solution of the interferon, or a dry lyophilized form of the interferon. The formulation in the sprayer can be aerosolized or not.

The term "systemic administration" as used herein means a form of administration of a drug that is intended for systemic circulation. Systemic administration includes injection into a blood vessel, injection into the lymphatic system, subcutaneous injection, intramuscular injection, intraperitoneal injection, or injection into a body cavity.

The term "treatment" shall include amelioration or relief of symptoms of a disease or illness or side effects thereof, or arrest of disease progression, as in inducing complete remission, partial remission, and stabilization of disease. In some instances, treatment includes prevention of recurrence or prolongation of tumor-free survival.

As used herein, the singular includes the plural and vice versa unless the context indicates otherwise. Also, the ranges of numbers provided herein include the specified beginning number and the specified ending number of each range and any number in between such ranges as if each such number in between has been specifically mentioned.

The invention is more particularly described as follows. These embodiments, however, are not intended to limit the scope of the claims, but serve to explain the invention to one of ordinary skill in the art to which this field applies. All references, patents, and other printed documents cited herein are incorporated herein by reference.

The inventors herein have discovered that cancers such as bone, skin, subcutaneous, mucosal and/or submucosal cancers, as well as bone pain arising from cancer in the bone, can be treated and the pain relieved by administration of a consensus interferon alpha that comprises anti-cancer activity and an amino acid sequence of SEQ ID NO:1.

In some embodiments, the consensus interferon alpha is encoded by a polynucleotide sequence of SEQ ID NO: 2. In some embodiments, the interferon comprises the super compound interferon, SIFN (also be referred to as recombinant super-compound interferon (rSIFN-co)), as prepared and as described in U.S. Pat. Nos. 7,364,724, 7,585,647, 8,114,395 and 8,287,852.

In some embodiments, the present interferon has the amino acid sequence of SEQ ID NO: 1. In some embodiments, the present interferon is encoded by the nucleotide sequence of SEQ ID NO: 2. In some embodiments, the present interferon has the amino acid sequence of SEQ ID NO: 1, and is encoded by the nucleotide sequence of SEQ ID NO: 2. Further, the interferon comprises the amino acid sequence of SEQ ID NO: 1, and is encoded by the nucleotide sequence of SEQ ID NO: 2.

In some embodiments, in comparison with interferon such as interferon alfacon-1 (INFERGEN®), which has the amino acid sequence of SEQ ID NO: 1, but is not encoded by the nucleotide sequence of SEQ ID NO: 2, the present interferon has a changed spatial configuration and/or enhanced biologic activities and/or different pharmacokinetics characteristics. For example, the present interferon has a changed spatial configuration and enhanced biologic activities, changed spatial configuration and different pharmacokinetics characteristics, or changed spatial configuration, enhanced biologic activities and different pharmacokinetics characteristics. The enhanced biological activities include: enhanced antiviral activity, enhanced tumor cell growth inhibition or proapoptotic effect, less side effects and/or could be used in large dose (e.g. each dose >10 million IU). For example, the enhanced biological activities can be enhanced antiviral activity and/or enhanced tumor cell (such as breast cancer cell or cervical cancer cell) growth inhibition or proapoptotic effect (see Zheng, J. et al. J Sichuan Univ (Med Sci Edi), 2010, 41(1), 29-34; Chen, Y, et al. J Sichuan Univ (Med Sci Edi), 2008, 39(5), 715-718). The different pharmacokinetics characteristics include: after intramuscular injection of the interferon in subjects whose BMI ranged from about 18 to about 23, the time of blood sample collection was plotted against the concentration of 2-5 A oligonucleotidase in the serum of the subjects, and the resulting area under the curve of this chart is significantly greater and/or the half-life of this interferon in the body is longer than those of the interferon such as interferon alfacon-1 (INFERGEN®), which has the amino acid sequence of SEQ ID NO: 1, but is not encoded by the nucleotide sequence of SEQ ID NO: 2 after injection under the same conditions.

In some embodiments, the present interferon has the amino acid sequence of SEQ ID NO: 1, and is encoded by the nucleotide sequence of SEQ ID NO: 2, wherein the interferon has increased inhibitory activities on the expression of hepatitis B surface antigen (HBsAg) and hepatitis B e antigen (HBeAg) of Hepatitis B Virus as compared to an interferon such as interferon alfacon-1 (INFERGEN®), which has the amino acid sequence of SEQ ID NO: 1, but is not encoded by the nucleotide sequence of SEQ ID NO: 2.

In some embodiments, the invention provides one or more methods and compositions for treatment of bone cancer in a subject, including primary or secondary bone cancer, where cancer cells are present in at least one bone or a part of a bone in a subject, using the fore-mentioned interferon.

In some embodiments, the invention provides one or more methods and compositions for treatment of skin or epithelial cancer in a subject, including primary and/or secondary skin cancer, using the fore-mentioned interferon. In some embodiments, the skin or epithelial cancer includes cervical carcinoma, basal cell carcinoma, epidermoid carcinoma, squamous cell carcinoma, carcinoma of the external genitalia, and melanoma, including melanocarcinoma.

In some embodiments, the invention provides one or more methods and compositions for treatment of subcutaneous cancer in a subject, including primary and/or secondary subcutaneous cancer, using the forementioned interferon. In some embodiments, the subcutaneous cancer includes prostatic carcinoma and breast cancer.

In some embodiments, the invention provides one or more methods and compositions for treatment of mucosal cancer in a subject, including primary and/or secondary mucosal cancer, using the fore-mentioned interferon. In some embodiments, mucosal cancer includes oral cancer, nasopharyngeal carcinoma, rectal cancer, laryngeal carcinoma and tongue cancer.

In some embodiments, the invention provides for methods and compositions for treatment of submucosal cancer in a subject, including primary and/or secondary submucosal cancer, using the fore-mentioned interferon.

In some embodiments, the invention provides methods and compositions for treating at least one of: bone cancer (primary or secondary), breast cancer, skin cancer, nasopharyngeal carcinoma, oral cancer, carcinoma of the vulva, prostatic carcinoma, cervical carcinoma and melanoma, including melanocarcinoma in a subject by administration of the interferon. In some embodiments, the interferon is administered to the subject by percutaneous administration. In some embodiments, the interferon is administered to the subject by transmucosal administration.

In some embodiments, the invention provides one or more methods and compositions for treatment of pain in a subject, such as pain arising from or associated with the presence of cancer, such as bone cancer pain, using the fore-mentioned interferon.

In some embodiments, the invention provides administering to the subject an effective amount of the interferon by administering the interferon locally such as on a cancer lesion, such as to or on the bone for cancer in the bones, the skin for skin cancer, the subcutaneous tissue for subcutaneous cancer, the mucosa for mucosal cancer, and the submucosa, for submucosal cancer, either directly or indirectly.

Such application can be direct, such as by perfusion when the bone, the subcutaneous tissue, or the submucosa is partially or totally exposed during surgery, or indirect, by application on the skin covering or in proximity to the bone (such as a cancer-affected bone) or the skin covering the subcutaneous cancer or on the mucosa surrounding the submucosa comprising a tumor, and allowing the interferon to pass through the skin or the mucosa.

In some embodiments, local administration of the interferon to a subject includes: percutaneous administration and/or transmucosal administration.

For local administration of the interferon by percutaneous administration, the interferon can be sprayed on the skin, such as the skin covering the cancer-affected tissue. In the case of bone cancer, the interferon can be sprayed on that part of the skin covering or in close proximity to the bone, such as the skin covering the humerus, the femur, the clavicle, etc., in which tumor cells, including metastatic tumor cells, can be found. In some embodiments, the interferon can be administered locally by transmucosal administration, where the interferon is applied to a mucosal surface affected by cancer, as the oral cavity for oral cancer.

In some embodiments, the interferon for percutaneous or transmucosal administration may be formulated as an aqueous solution, or a cream that can be applied to the skin or mucosa, or a membrane permeation or diffusion drug delivery system, or a controlled release drug delivery system, or a closed drug delivery system, or a patch such as a transdermal patch, or a depot comprising the interferon for injection under the skin to produce a slow- or controlled-release effect, as desired.

In some embodiments, interferon for percutaneous administration or transmucosal administration can be in the form of a solution or a suspension. The solution or suspension will comprise an amount of the interferon and other pharmaceutically acceptable agents or excipients conventionally used, such as water, phosphate buffered saline, EDTA, Tween 80, trisodium citrate, glycerol, sodium chloride, phenylmethanol, HSA and the like. Such a solution can be made, for example, as described in U.S. Pat. No. 7,585,647.

The interferon herein for local administration or for inhalation can be formulated as a spray, such as one that can be sprayed on the skin, or on the mucosa, or on an exposed cancer-affected tissue, or into the nose for intranasal delivery, or into the nasopharynx for pulmonary delivery.

The interferon herein can also be formulated as a dry, lyophilized powder. The dry powder can be used in an aerosolized spray for administration to the nose or to the lungs such as through the nasopharynx.

The interferon herein can further be applied in the form of a transdermal patch comprising a solution or suspension of the interferon for either fast or slow or controlled release of the interferon. The transdermal patch herein can be made using standard or extant technology, for example, as described in U.S. Pat. Nos. 8,158,145, 8,095,213 and 8,071,125, and the like. The transdermal patch can be placed on the cancer-affected skin, or on the skin covering the cancer-affected tissue.

In some embodiments, the transdermal patch that can be applied to the skin covering the affected area of the bone and can be left in place over a period of time, such as for several hours, for one or a few days.

The interferon herein can further be formulated as encapsulated particles, whether made from a single or composite material. Examples of such particles are nanoparticles, microparticles, microspheres, liposomes and the like, using extant technology. Such particles can be made, for example, as described in U.S. Pat. Nos. 7,537,803, 8,389,493 and 7,829,113.

In some embodiments, the cancer in the bone, or skin or subcutaneous cancer, or mucosal cancer or submucosal cancer can be a primary cancer or a metastasized tumor originating from a primary tumor arising from another tissue or organ.

In some embodiments, the primary tumor herein can be any one or more of: a solid tumor and a non-solid tumor.

In some embodiments, the primary tumor herein includes at least one of: cancer of the respiratory system, cancer of the digestive system, cancer of the urinary system, breast cancer, skin cancer, subcutaneous cancer, mucosal cancer, submucosal cancer, cancer of the reproductive system, head and neck cancer, cancer of the hormonal system, and cancer of the nervous system.

In some embodiments, the cancer of the digestive system includes at least one of: oral cancer, tongue cancer, laryngeal carcinoma, esophageal cancer, gall bladder cancer, liver cancer, gastrointestinal cancer, and pancreatic cancer, the cancer of the reproductive system includes at least one of: carcinoma of the external genitalia, cervical cancer, endometrial cancer, uterine cancer, ovarian cancer, and prostate cancer; the cancer of the respiratory system includes at least one of: lung cancer and nasopharyngeal carcinoma; the cancer of the urinary system includes at least one of: kidney cancer and bladder cancer; the cancer of the hormonal system includes at least one of: adrenal cancer and thyroid cancer; the head and neck cancer includes nasopharyngeal carcinoma; the skin cancer includes at least one of: basal cell carcinoma, epidermoid carcinoma, squamous cell carcinoma, carcinoma of the external genitalia, and malignant melanoma; the subcutaneous cancer includes prostatic carcinoma and breast cancer, the mucosal cancer includes cancer involving the mucosa, such as oral cancer, tongue cancer, gastrointestinal cancer, and colorectal cancer; the submucosal cancer includes bone cancer, and the cancer of the nervous system includes at least one of: neuroma, malignant neuroma, glioma, and astrocytoma.

In some embodiments, the lung cancer includes at least one of: small cell lung cancer and non-small cell lung cancer; the gastrointestinal cancer includes at least one of: gastrointestinal interstitial cell tumor, stomach cancer, colon cancer, rectal cancer, and colorectal cancer, the gall bladder cancer includes cholangiocarcinoma; the liver cancer includes hepatocellular carcinoma; the kidney cancer includes renal cell carcinoma; the bladder cancer includes superficial bladder cancer, and the subcutaneous cancer includes at least one of: prostatic carcinoma and breast cancer.

In some embodiments, the primary tumor herein comprises at least one of: a carcinoma, a sarcoma, and a rhabdomyosarcoma.

In some embodiments, the primary tumor herein can be at least one of: abdominal tumor, myoepithelial carcinoma, synovial sarcoma, hemangioma, lymphoma and Kaposi's sarcoma.

In some embodiments of the invention, the interferon can be administered both locally, such as percutaneously and/or transmucosally and systemically to the subject.

In some embodiments, the invention provides methods and compositions for the treatment of cancer in the bone, skin cancer, subcutaneous cancer, mucosal cancer and/or submucosal cancer in a subject comprising administering to the subject an effective amount of a consensus interferon alpha that comprises anti-cancer activity, wherein the interferon is administered both by systemic administration, and by percutaneous administration.

In some embodiments, the systemic administration includes injection into the subject. Injection herein includes injection in at least one of the following modes: intramuscularly, intratumorally, intraperitoneally, intravenously, subcutaneously, into the thoracic cavity, and into one or more lymph nodes.

In some embodiments, the invention provides methods and compositions for the treatment of cancer as any of the foregoing methods and compositions which, besides administering the interferon by systemic administration, such as by injection, and such as by intramuscular injection, and by percutaneous administration, such as by spraying on a cancer-affected tissue, the interferon is additionally administered by inhalation.

In some embodiments, the invention provides methods and compositions for the treatment of cancer in bone, skin cancer, subcutaneous cancer, mucosal cancer, and/or submucosal cancer in a subject comprising administering to the subject an effective amount of a consensus interferon alpha that comprises anti-cancer activity, wherein the interferon is administered both by inhalation and by percutaneous administration to the cancer-affected tissue.

In some embodiments, inhalation includes inhalation through the nose or through the throat/nasopharynx to the lungs. Administration by inhalation through the nose can be accomplished with an intranasal spray. Administration by inhalation through the throat/nasopharynx to the lungs can be accomplished by use of inhaler. Such intranasal spray or inhaler can be in the form of an aerosolized formulation of the interferon or an aqueous solution containing the interferon, for example.

In some embodiments, the invention provides methods and compositions as any described herein, where the interferon administered locally includes applying the interferon to one or more cancerous lesions. Further, application to the cancerous lesion can be by infiltration administration, percutaneous administration, transdermal administration, epidermal administration, and transmucosal administration. Local administration can be achieved by spraying the interferon locally.

In some embodiments, the invention provides methods and compositions as any described herein, where the interferon formulated for local administration can be formulated as at least one of: an aqueous solution, a dry powder, or a cream.

In some embodiments, the invention provides any one or more of the methods and compositions described herein, wherein application of the interferon by percutaneous administration, in combination with application of the interferon by systemic administration, such as by injection, and such as by intramuscular injection, and/or administration by inhalation, can be administered on the same day or on separate days.

In some embodiments, application of the interferon by percutaneous administration can be before, simultaneously or at about the same time as, or after administration of the interferon by injection or by inhalation, if any.

In some embodiments, the invention provides any one or more of the methods and compositions as described herein, where application of the interferon to the mucosa comprises submucosal administration.

In some embodiments, the interferon that is applied locally, percutaneously or transmucosally, such as by spraying, can be applied in a range of about 1 to 12 times a day, optionally in a range of about 2-10 times a day, still optionally, in a range of about 3-8 times a day, further optionally, in a range of about 4-7 times a day. In some embodiments, the interferon that is applied locally, percutaneously or transmucosally is applied 4 or 5 or 6 times a day.

In some embodiments, the interferon that is applied locally, percutaneously or transmucosally, such as by spraying, can be applied at least 1, 2, 3, 4, 5, 6, 7, or 8, or more times per day.

In some embodiments, the invention provides methods and compositions as any described herein, where local administration, administration to the bone, skin, mucosal or submucosa comprises applying a formulation of the interferon at a concentration in a range of about 0.01 mg/ml to about 5 mg/ml, optionally, in a range of about 0.03 mg/ml to about 2 mg/ml, further optionally in a range of about 0.05 mg/ml to about 1 mg/ml, and still further optionally, in a range of about 0.1 mg/ml to about 0.5 mg/ml. In some embodiments, the interferon for local administration comprises interferon in a range of about 2 microgram to about 2100 microgram, optionally, in a range of about 4 microgram to about 1800 microgram, still optionally, in a range of about 9 microgram to about 15 microgram, further optionally, in a range of about 12 microgram to about 1200 microgram, yet still optionally, in a range of about 15 microgram to about 1000 microgram, yet further optionally, in a range of about 18 microgram to about 900 microgram, yet still optionally, in a range of about 21 microgram to about 750 microgram, and still further optionally, in a range of about 24 microgram to about 600 microgram.

The invention additionally provides, in some embodiments, administration of the interferon locally every day or every other day. In some embodiments, the interferon, for local administration, is administered every $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, or $21^{st}$ day. In some embodiments, the interferon administered locally is administered every month, every 2, or 3, or 4, or 5, or 6, or 7, or 8, or 9, or 10, or 11, or 12 months, or longer, such as for the remaining life of the subject.

In some embodiments, the invention provides methods and compositions as any described herein, where the interferon is applied by spraying, and the interferon in the spray can be in an amount in a range of about 6 microgram to about 100 microgram, optionally, in a range of about 10 microgram to about 80 microgram, still optionally, in a range of about 20 microgram to about 60 microgram, further optionally, in a range of about 30 microgram to about 40 microgram per spray administration.

In some embodiments, the interferon for spray administration comprises a concentration in a range of about 0.01 mg/ml to about 5 mg/ml, optionally in a range of about 0.03 mg/ml to about 2 mg/ml, further optionally, in a range of about 0.05 mg/ml to about 1 mg/ml, and still further optionally, in a range of about 0.1 mg/ml to about 0.5 mg/ml.

In some embodiments, the interferon that is formulated for injection can be injected every day or every other day or every few days, such as every 2 or every 3 days. In some embodiments, the interferon is administered systemically is administered at least once every 1-8 days, optionally, at least once every 2-7 days, still optionally, at least once every 3-6 days, further optionally, at least once every 4-5 days, still further optionally, at least once every 1-2 days.

In some embodiments, the interferon to be administered by systemic administration, such as by injection, and such as by intramuscular injection, is administered in an amount in a range of about 2 microgram to about 70 microgram, optionally in a range of about 4 microgram to about 50 microgram, further optionally, in a range of about 9 microgram to about 30 microgram, still optionally, in a range of about 15 microgram to about 24 microgram, still further optionally, in a range of about 18 microgram to about 21 microgram, per injection.

In some embodiments, the second dose of interferon that is injected can be at a higher dosage than the first dose. In some embodiments, the third dose of interferon for injection can be the same as the second dose or can be higher than the second dose.

In some embodiments, for systemic administration, the interferon is administered in at least one initial dose, that is, an induction dose, in a range of about 2 microgram to about 15 microgram, optionally, about 3 microgram to about 12 microgram, still optionally about 4 microgram to about 9 microgram, further optionally, about 5 microgram to about 6 microgram. In some embodiment, the induction dose has about 9 microgram or about 15 microgram of the interferon. The induction dose can be used for one or more subsequent administrations to the subject as well.

In some embodiments, for systemic administration, the interferon is further administered in at least one subsequent therapeutic dose in a range of about 10 microgram to about 50 microgram each time, optionally in a range of about 12 microgram to about 30 microgram each time, further optionally in a range of about 15 microgram to about 24 microgram each time, and still optionally, in a range of about 18 microgram to about 21 microgram each time. In some embodiments, the therapeutic dose has about 15, or 18, or 21 microgram of the interferon.

In some embodiments, the interferon to be administered by systemic administration is administered at least for: 1 day, 2 days, 3 days, 4 days, 5 days, 6 days, 7 days, 8 days, 9 days, 10 days, 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, 3 years, 4 years, 5 years, and 6 years.

In some embodiments, the interferon to be administered by systemic administration is administered for a duration in a range of about 1 day to about 6 years, optionally, about 1 week to about 4 years, still optionally, about 2 weeks to about 3 years, further optionally, about 1 month to about 1 year, still further optionally, about 2 months to about 9 months, or longer, such as throughout the remaining life of the subject.

In some embodiments, the interferon for systemic administration is administered to the subject at a frequency in a range of about once every 1-7 days, further optionally, about once every 1-2 days, at the induction dose. In some embodiments, the interferon for systemic administration is administered at a frequency of about once every day or about once every other day at the induction dose. Optionally, the interferon for systemic administration is administered every 2, 3, 4, 5, 6, 7, 8, 9, or 10 days at the induction dose.

In some embodiments, for systemic administration, the interferon is administered to the subject at a frequency in a range of about once every 1-7 days, further optionally, about in a range of about once every 1-2 days, at the therapeutic dose.

In some embodiments, for systemic administration, the interferon is administered to the subject at a frequency of about once every day, or about once every 2, 3, 4, 5, 6, 7, 8, 9, or 10 days, at the therapeutic dose.

In some embodiments, the interferon is administered by subcutaneous or intramuscular injection at least 2 times, optionally, at least 4 times, further optionally, at least 6 times, still optionally, at least 8 times, still further optionally, at least 10 times.

In some embodiments, for systemic administration, the time interval between administration of the induction dose and the administration of the therapeutic dose of the interferon is in a range of about 1 day to about 1 month, optionally or preferably, in a range of about 1 day to about 1 week, still optionally or more preferably, in the range of about 1 day to 3 days. In some embodiments, the time interval between the induction dose and the therapeutic dose is 1 day, 2 days, 3 days, 4 days, 5 days, 6 days, 7 days, 8 days, 9 days, 10 days, 1 week, 2 weeks, 3 weeks, or 1 month.

In some embodiments, the time interval between injection of the first dose and injection of the second dose of interferon is in a range of about 1 day-1 month, optionally, in a range of about 2 days to about 3 weeks, further optionally, in a range of about 3 days to about 2 weeks, still optionally, in a range of about 4 days to about 10 days, still further optionally, in a range of about 5 days to about 9 days, yet further optionally, in a range of about 6-8 days, and still further optionally, about 7 days.

In some embodiments, the duration of administration of the induction dose and the therapeutic dose is at least: 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, or 6 years, or optionally longer or over the remaining life of the subject.

In some embodiments, the inhalation administration of the interferon includes at least one of: pulmonary inhalation and nasal inhalation.

In some embodiments, the interferon for inhalation administration includes at least one of: dry powder and aerosolized interferon.

In some embodiments, the interferon to be applied by inhalation is administered in an amount in a range of about 100 microgram to about 2000 microgram, optionally, about 120 microgram to about 1500 microgram, further optionally, about 150 microgram to about 1200 microgram, still optionally, about 200 microgram to about 900 microgram, yet further optionally, about 450 microgram to about 750 microgram, still further optionally, about 500 microgram to about 650 microgram, in one inhalation administration. In some embodiments, the interferon to be applied by inhalation is administered in an amount of 600 microgram in one inhalation administration.

In some embodiments, the interferon for inhalation administration is administered by inhalation administration about once every 1 or 2 or 3 days, optionally, every day.

In some embodiments, the duration of inhalation administration is in a range of about 1 day to about 6 years, optionally, about 1 week to about 4 years, further optionally, about 2 weeks to about 3 years, still optionally, about 3 weeks to about 2 years, still further optionally, about 1 month to about 1 year, or yet further optionally, about 2 months to about 9 months.

In some embodiments, the duration of inhalation administration is at least for 1 day, 2 days, 3 days, 4 days, 5 days, 6 days, 7 days, 8 days, 9 days, 10 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, or 6 years, or optionally for a long time, such as over the remaining life of the subject.

In general, the duration and frequency of administration of the interferon herein can be determined by one or more attending physicians or medical staff depending on the typical criteria such as the need of the subject for further treatment, the health of the subject, the tolerance of the subject to the interferon, the presence of adverse side effects, and the like.

In some embodiments, the interferon administration is the sole anti-cancer therapy administered to the subject. In some embodiments, the interferon administration is combined with at least one other anti-cancer therapy.

The at least one other anti-cancer therapy can be administered to the subject before, at about the same time, and/or after administration of the interferon.

In some embodiments, the at least one other anti-cancer therapy includes at least one of: chemotherapy, radiotherapy, surgical therapy, interventional therapy, biotherapy, targeted therapy, and Traditional Chinese medicine.

In some embodiments, the biotherapy includes the use of any type of biologics for treatment and includes recombinant proteins, antibodies, gene therapy, cell therapy, use of targeted antibodies, or other immunotherapy.

In some embodiments, the surgical therapy comprises ablation therapy. In some embodiments, the at least one anti-cancer therapy is a non-surgical therapy.

In some embodiments, the invention provides treatment which achieves at least one of: elimination of at least one cancer lesion, reduction in size of at least one cancer lesion, and non-progression of growth of at least one cancer lesion, as compared to before treatment.

The invention provides in some embodiments, a sprayer for administering an interferon that comprises anti-cancer activity and an amino acid sequence of SEQ ID NO: 1.

In some embodiments, the interferon in the sprayer is formulated in an amount for administering the interferon at least 1-12 times, optionally, 2-10 times, further optionally, 3-8 times. In some embodiments, the sprayer herein contains an amount of the interferon for administering the interferon at least 4 or 5 or 6 times.

In some embodiments, the amount of interferon in the sprayer has a concentration in a range of at least about 0.01 mg/ml to about 5 mg/ml, optionally, about 0.03 mg/ml to about 2 mg/ml, still optionally, about 0.05 mg/ml to about 1 mg/ml. In some embodiments, the sprayer contains the interferon at a concentration of about 0.1 mg/ml, about 0.2 mg/ml, about 0.3 mg/ml, about 0.4 mg/ml, or 0.5 mg/ml.

In some embodiments, the sprayer is described herein and is a single use sprayer containing one day's supply of the interferon. In some embodiments, the sprayer is a multi-use sprayer and contains interferon sufficient for use for at least 2 days, or 3 days, or 4 days, or 5 days, or a week, or 2 weeks.

In some embodiments, the invention provides a sprayer as any described herein, where the sprayer is configured and the interferon therein is formulated for delivery of the interferon to the nose of the subject.

In some embodiments, the sprayer herein is configured and the interferon therein is formulated for delivery of the interferon to or on at least the subject's skin, or bone, or mucosa of the subject.

In some embodiments, the sprayer herein is configured and the interferon therein is formulated for delivery of the interferon by inhalation to the lungs of the subject.

The invention further provides a measured or metered dose of an interferon comprising an amount of the interferon, wherein the interferon comprises anti-cancer activity and an amino acid sequence of SEQ ID NO: 1.

A metered dose allows the subject to self-administer the interferon and/or allows administration by non-medical, lay staff, such as by one of the patient's family members, thus, reducing the number of visits to the hospital or to the doctor's office, and cutting down costs of treatment. The inventors' discovery of the effectiveness of local administration of the interferon, such as by percutaneous or transmucosal administration, such as by spraying on a cancer-affected area, with or without additional systemic administration of the interferon, and with or without additional inhalation administration of the interferon, makes such delivery and such administration feasible.

In some embodiments, the metered dose contains the interferon in an amount in a range of about 100 microgram to about 2000 microgram, optionally, about 120 microgram to about 1500 microgram, further optionally, about 150 microgram to about 1200 microgram, still optionally, about 200 microgram to about 900 microgram. In some embodiments, the metered dose optionally or preferably contains the interferon in an amount in a range of about 450 microgram to about 750 microgram, still optionally or preferably, in a range of about 500 microgram to about 650 microgram. In some embodiments, the metered dose contains the interferon herein in an amount of about 600 microgram.

In some embodiments, the metered dose contains a single use amount of the interferon. In some embodiments, the metered dose contains an amount of the interferon that is sufficient for 2 treatments, 3 treatments, 4 treatments or 5 treatments. Optionally, the metered dose contains at least a one-week supply of the interferon.

In some embodiments, the metered dose is formulated for percutaneous administration, such as for local spraying. In some embodiments, the metered dose is formulated for inhalation. In some embodiments, the metered dose is formulated for inhalation via the nose. In some embodiments, the interferon is formulated for inhalation via the lungs.

In some embodiments, the metered dose contains the interferon in lyophilized powder form. In some embodiments, the interferon in the metered dose is aerosolized. In some embodiments, the interferon in the metered dose contains an aqueous formulation of the interferon, or interferon in the form of nanoparticles, microparticles, or microspheres and the like.

The invention further provides a transdermal patch comprising the consensus interferon alpha that comprises anti-cancer activity, and having an amino acid sequence of SEQ ID NO: 1.

The invention also provides a method of preparation of a medicament for administration to a subject, where the medicament contains the consensus interferon alpha that has anti-cancer activity and an amino acid sequence of SEQ ID NO: 1. The medicament containing the interferon can be used for treatment of cancer in the bones, skin cancer, subcutaneous cancer, mucosal cancer, and submucosal cancer, as described herein. The medicament can be formulated in at least 2 distinct formats, one for systemic administration, such as by injection and the other for local administration, such as application to the skin, bone, or mucosa of the subject.

In some embodiments, the fore-mentioned medicament can be formulated in a third format for inhalation administration, such as a nasal spray or an aerosolized form for pulmonary delivery.

The invention further provides, in some embodiments use of a consensus interferon alpha that comprises anti-cancer activity and an amino acid sequence of SEQ ID NO; 1, in the preparation of a medicament for treatment of bone cancer, skin cancer, subcutaneous carcinoma, mucosal carcinoma and/or submucosal carcinoma in subjects. In some embodiments, the invention provides the use of such interferon in preparation of a medicament for treatment of pain, such as that associated with or arising from cancer in the bones, such as in bone cancer.

The invention moreover provides a pharmaceutical composition that contains the fore-mentioned interferon and at least one pharmaceutically acceptable carrier or excipient, where the composition is formulated for local administration, for systemic administration, and/or for inhalation administration, for the treatment of bone cancer, skin cancer, subcutaneous carcinoma, mucosal carcinoma and/or submucosal carcinoma in subjects.

In some embodiments, the invention provides a pharmaceutical composition that contains the fore-mentioned interferon and at least one pharmaceutically acceptable carrier or excipient, where the composition is formulated for treatment of pain, such as bone pain associated with or arising from cancer, such as bone cancer.

In some embodiments, the interferon herein is encoded by a polynucleotide comprising the sequence of SEQ ID NO: 2.

In one embodiment, the present invention provides a method of treatment of cancer in bone in a subject and/or bone pain in a subject who has cancer in bone, the method comprises administering to the subject an effective amount of an interferon that comprises anti-cancer activity, and the interferon comprises an amino acid sequence of SEQ ID NO: 1.

In one embodiment, the cancer in bone is a primary bone cancer, or a secondary bone cancer that metastasized from a primary tumor.

In one embodiment, the interferon is administered to the subject by local administration.

In one embodiment, the local administration of the interferon comprises administering the interferon to the cancerous lesion, or the interferon is administered by local administration to an area affected by cancer or comprising cancer cells. In another embodiment, the local administration of the interferon comprises at least one of infiltration administration, percutaneous administration, transdermal administration, epidermal administration, and transmucosal administration.

In one embodiment, the administration of the interferon to the subject comprises administration of the interferon to or on the bone, the skin, the mucosa, and/or the submucosa of the subject, and the interferon comprises a concentration in a range of about 0.01 mg/ml to about 5 mg/ml.

In one embodiment, the local administration of the interferon comprises administration by spraying. In one embodiment, application of interferon to the skin comprises application to or on the skin in proximity to the bone affected by cancer, or application to or on the skin surrounding the bone affected by cancer. In one embodiment, the application of interferon to the mucosa comprises an application to the mucosa in proximity to the bone affected by cancer, or application to the mucosa surrounding the bone affected by cancer.

In one embodiment, the local administration of the interferon comprises administration of interferon in a range of about 2 microgram to about 2100 microgram. In one embodiment, the administration of the interferon by spraying comprises administration of the interferon in an amount in a range of about 6 microgram to about 100 microgram per spray administration.

In one embodiment, the interferon for local administration is formulated as at least one of a dry powder, an aqueous solution, a cream, a membrane permeation or diffusion drug delivery system, a controlled release drug delivery system, a closed drug delivery system, a transdermal patch, or a depot comprising the interferon injected under the skin, for producing a slow-release effect. In another embodiment, the interferon is formulated as nanoparticles, microparticles, microsphere, liposomes or a controlled release single or composite material.

In one embodiment, administering the interferon to the subject further comprises administering the interferon by systemic administration and/or inhalation administration.

In one embodiment, the method further comprises administering to the subject at least one other anti-cancer therapy, and the other anti-cancer therapy is administered to the subject before, at about the same time, and/or after administration of the interferon. In one embodiment, the at least one other anti-cancer therapy is chemotherapy, radiotherapy, surgical therapy, interventional therapy, biotherapy, targeted therapy, or Traditional Chinese medicine. In one embodiment, the biotherapy comprises at least one of gene therapy and immunotherapy, and the surgical therapy comprises ablation therapy.

In one embodiment, the present invention provides a method of treatment of skin cancer, subcutaneous cancer, mucosal carcinoma and/or submucosal carcinoma and/or pain associated with the cancer in a subject, the method comprises administering to the subject an effective amount of an interferon that comprises anti-cancer activity, and the interferon comprises an amino acid sequence of SEQ ID NO: 1.

In one embodiment, administering the interferon to the subject comprises administering the interferon by local administration.

In one embodiment, the local administration of the interferon comprises at least one of infiltration administration, percutaneous administration, transdermal administration, epidermal administration, and transmucosal administration.

In one embodiment, the application of interferon comprises application of the interferon percutaneously, on or to the skin of the subject, and/or transmucosally, to or on the mucosa of the subject.

In one embodiment, the local administration of the interferon comprises administration by spraying. In another embodiment, the administration of the interferon to the subject further comprises administering the interferon by systemic administration and/or inhalation administration.

In one embodiment, the method further comprises administering to the subject at least one other anti-cancer therapy, and the anti-cancer therapy is administered to the subject before, at about the same time, and/or after administration of the interferon.

In one embodiment, the present invention provides a sprayer for administering an interferon that comprises anti-cancer activity and an amino acid sequence of SEQ ID NO:1, and the sprayer comprises the interferon formulated for local administration of the interferon. In one embodiment, the interferon is formulated at a concentration in a range of at least about 0.01 mg/ml to about 5 mg/ml. In another embodiment, the interferon is formulated at a concentration of about 0.3 mg/ml.

The invention herein is further exemplified by the following examples which are for illustrative purposes and are not to be construed as limiting the invention in any way.

Example 1. Treatment of Patient #1 with
Non-Small-Cell Lung Cancer (NSCLC) and
Multiple Bone Metastases Summary. Patient #1 was a 39 year old male who was diagnosed with NSCLC with multiple lymph node metastases in the mediastinum, the left segment of his neck, the right and root segment of his neck, left supraclavicular fossa. Patient #1 also had left-sided pleural effusion and multiple bone metastases in the vertebral column, bilateral ribs, right clavicular joint, sternum, left sacrum, etc. Patient #1 was given intramuscular injection and aerosol inhalation of SIFN (or recombinant super-compound interferon (rSIFN-co)) and local spraying of the SIFN on bony lesions, in combination with chemotherapy treatment, a GP regimen, and Gefinitib therapy. After treatment, the primary lesions on the left lung disappeared as well as the multiple lymph node metastases in the left supraclavicular fossa and left-sided pleural effusion. Also, metastatic bone lesions around the whole body shrank or disappeared.

Treatment with SIFN began on Oct. 12, 2011 with aerosol inhalation of 600 ug every day. Intramuscular injection of SIFN started on Dec. 12, 2011, once every other day at 9 μg dose for the first time, 15 μg dose for the second time and 18 μg dose for the third time and thereafter. Local spraying on bone metastases (vertebral column, ribs, sternum, sacrum, etc.), by spraying on the skin over the bone metastases, began on Mar. 12, 2012 at about 4 to 6 times per day.

A second cycle of GP Regimen started on Oct. 14, 2011 (each cycle lasting 21 days) at 1000 mg/m$^2$ of Gemcitabine on days 1 and 8 and 75 mg/m$^2$ of Cisplatin on day 1. Gefinitib was administered from November 2011 at 1 pill each time (250 mg/pill) and once per day.

Diagnosis before administration of SIFN. A chest CT scan on Sep. 21, 2011 showed a high-density blocky shadow (9 cm×3.5 cm) around the left mediastinum with a CT value of 39 Hu. The boundaries between this shadow and part of the great vessels in the mediastinum superius, left hilum and left posterior pleura were obscure. Patchy shadow of inflammatory exudates with high density could be seen in the lungs.

Enlarged lymph nodes were found in the mediastinum. A few patchy shadows with high density were seen inhomogeneously in the upper segment of the right hilum portion, where the boundaries were clear. Arched effusions were found on left posterior side. Diagnosis conclusion: Patient #1 had lung cancer in left mediastinum combined with left sided pleural effusion and obstructive pneumonia. Multiple patchy shadows were present in the hilum, suggesting the possible occurrence of metastases.

Biopsy was conducted with fibro-bronchoscopy on Sep. 27, 2011. A biopsy was done in the bronchus of the left upper lobe. Three grey soft tissues were found with about 0.1 cm×0.1 cm×0.1 cm in size. Diagnosis conclusion: Patient #1 might have poorly or moderately differentiated adenocarcinoma.

The whole body bone ECT scan on Sep. 29, 2011 showed multiple lesions with high radioactivity concentration in the vertebral column, bilateral ribs, right-sided sternoclavicular joints, sternum, left-sided sacroiliac joints and left-sided ilium. Radioactivity distribution was normal in the skull and limb long bones. Diagnosis conclusion: Systemic bone lesions with high radioactivity concentration were found, suggesting possible occurrence of systemic bone metastases.

Color Doppler ultrasound was conducted on Sep. 30, 2011. Multiple hypoechoic nodules were found at the left segment of the neck, which had clear boundaries without any hilum of lymph node. Larger hypoechoic nodule was 1.0 cm×0.7 cm in size. One hypoechoic nodule of about 1.2 cm×0.8 cm was found at the left supraclavicular fossa, which had clear boundary but had no hilum of the lymph node. One hypoechoic nodule of about 1.4 cm×1.1 cm was seen at the root segment of right-sided neck, which had clear boundary but had no hilum of the lymph node. No abnormal lymph nodes were found in the right-sided supraclavicular fossa. Diagnosis conclusion: hypoechoic nodules and abnormal lymph nodes were found at left segment of neck, left supraclavicular fossa and root segment of the right-sided neck.

Diagnosis after administration of SIFN.

The CT scan on Nov. 15, 2011 showed shadows of soft tissues of about 3.6 cm×4.2 cm in the left upper lung. High density patchy shadows were scattered and had obscure boundaries. No enlarged lymph nodes were seen in the mediastinum.

A bone scan was conducted on Dec. 6, 2011. Multiple spot-like, mass-like and sheet-like shadows with abnormal radioactivity concentration could be seen in right sternoclavicular joints, ribs, vertebral column and pelvis. Radioactivity distributions of other parts were substantially uniform and symmetrical. Diagnosis conclusion: partial lesions shrank and were reduced as compared to the previous CT result (Sep. 29, 2011).

PET/CT scan was conducted on Dec. 29, 2011. A nodule with a diameter of about 8 mm was observed at the apex of the left lung and the radioactivity distribution was slightly increased. Small sheet-like shadows with slightly higher density and fibrous lesions were found in surrounding area of the lung and radioactivity distribution was slightly increased. Scattered, patchy shadows with slightly higher density were found in the lung and no significant abnormalities were found in the radioactivity distribution.

Conclusion: (1) after treatment, no obvious increase in FDG metabolism was found on or at lesions of the apex of the left lung, suggesting inactivation of most of the tumor cells; (2) asymmetric hyperosteogeny was found in several parts of the whole body and FDG metabolism in some lesions was inhomogeneous with a few increased. After treatment for 2 months, the patient had lesions in his lungs disappeared and the systemic bone metastases shrank in size.

PET/CT scan on May 31, 2012 only indicated that, the bone density changed in several vertebrae of the spinal column and shadows with abnormal radioactivity concentrations were found, while the bone metastases disappeared.

Example 2. Treatment of Patient #2 with Melanoma and Bone Metastases

Patient #2 was a 43 year old female who had melanoma at the nose (recurrence after surgery) and bone metastases at the bilateral hip joints, bilateral femurs, bilateral humeri, ribs and bilateral shoulder joints. Intramuscular injection of SIFN and local spraying of SIFN on lesions (on the skin over the bone metastases) were administered. After treatment, the lesions disappeared, including those involving the bilateral shoulder joints, the multiple enlarged lymph nodes in the armpits, the recurrent and metastatic lesions at residual cavity after surgery of the right paranasal sinus and nasal cavity. The multiple abnormal signals at the bilateral hip joints and upper segment of the femur also disappeared.

Treatment regimens before administration of SIFN.

Two cycles of administration of Endostar and temozolomide were applied on Oct. 30, 2011 and Nov. 30, 2011. Endostar at 15 mg was given per day on days 1-10 and 200 mg of temozolomide was given per day on days 1-5 orally.

Targeted radiotherapy (50 Gy/25f) began on Nov. 2, 2011 and the target regions included right maxillary sinus and ¼ of the left maxillary sinus, bilateral ethmoid sinuses, bilateral frontal sinuses and the adjacent tissues of the right eyeball. Radiotherapy ended on Dec. 7, 2011.

Administration of SIFN.

Treatment with SIFN began on Dec. 21, 2011. Intramuscular injection of SIFN was administered every other day (9 μg for the first time, 15 μg for the second time, 18 μg for the third time and thereafter) combined with local spraying to the skin surface of the right shoulder for 4 to 5 times per day. Spraying was applied to the skin surfaces of the left shoulder and other regions of bone metastases from Feb. 27, 2012 at 4 to 5 times per day.

Diagnosis before administration of SIFN.

Surgery for the right sinus was provided using an endoscope and the neoplasm in the nasal cavity was resected on Aug. 23, 2011. Biopsy after surgery showed that tumors were found in the polyp-like matter in the middle nasal meatus and the mass inside the right maxillary sinus. Malignant melanoma was diagnosed by immunohistochemistry: HMB45 (partly+), MART1 (−), S100 (−), CD63(+), NSE(−), PCK (−), EMA (+), CD56(−), and KI671(25%). Subtotal resection of right maxillary bone and resection of the tumor in the nasal cavity and paranasalsinus was conducted again on Oct. 8, 2011.

MRI of paranasalsinus was conducted on Dec. 8, 2011. 1. Compared with the imaging taken on Oct. 26, 2011, soft tissues surrounding residual cavity were thickened and significantly enhanced, suggesting a possibility of recurrence. 2. Several lymph nodes at the neck were enlarged. 3. Hypertrophy was found at the left-sided inferior nasal concha and inflammation was seen at the left maxillary sinus, sphenoid sinus and ethmoid sinus. 4. Otitis media and mastoiditis were found at the right side.

The MRI scan of the hip joints on Dec. 8, 2011 showed that a lesion with long T1 and long T2 signal was seen at the left acetabulum and extended to the left ischium. High signals in fat suppression sequences and significant enhancement were found. Significantly enhanced long T1 and long T2 nodular lesion were seen at the lower portions of bilateral ilia and right anterior acetabulum. Conclusion: multiple abnormal signals were found in the bone substance of the bilateral hip joints and bone metastases probably occurred.

MRI of shoulder joints on Dec. 8, 2011 showed that, patchy shadows with long T1 and long T2 signals, inhomogeneous enhancement and obscure boundaries were found at the bilateral acromial ends of the clavicles, infraglenoid bone substance of the right scapula, peripheral margin of the bilateral scapulae, the upper parts of the bilateral humeri and bilateral multiple ribs. Multiple lymph nodes appeared at bilateral axilla with part of them enlarged. Conclusion: considering the medical history, the description above indicated multiple metastases to bilateral shoulder joints and axilla.

Bone imaging on Dec. 12, 2011 showed that, bones of the whole body were displayed clearly and dense radioactive patchy shadows were found in the nasopharyngeal region, maxillary sinus region, T8 vertebra and the lower segment of the left acetabulum. Diagnosis conclusion: multiple lesions with elevated bone metabolism were found, suggesting possible occurrence of bone metastases.

Diagnosis after administration of SIFN.

MRI scan of the shoulder joint on May 2, 2012 showed no obvious bone destruction at the left shoulder. Spot-like shadows with long T2 and long T1 signals were seen in the humeral head, probably indicating small cystic lesions.

Pelvic MRI on May 2, 2012 showed shadows with long T1 and long T2 signals at the upper branch of the left pubis with significant enhancement. No obvious abnormality was seen in the remaining part of the pelvis.

Brain MRI on May 2, 2012 showed 1) no intracranial abnormality; 2) bilateral otitis media and mastoiditis; 3) the middle and inferior turbinates, the inner wall of maxillary sinus at the right side were missing, leading to a cavity formed by connecting sinus cavity and nasal cavity; 4) left maxillary sinusitis; 5) sphenoid sinusitis and frontal sinusitis.

MRI of lumbar, head and shoulder joints on Jun. 26, 2012 showed that: 1) fat deposition was found on rear and upper portion of the second lumbar vertebra with the remaining corpus vertebrae and intervertebral disc being normal; 2) intracranial brain tissue was normal; 3) the lack of nasal conchae at the right nasal cavity and inner wall of the right maxillary sinus was as above; 4) bilateral ethmoiditis and sphenoid sinusitis and bilateral mastoiditis were found; 5) no lymph nodes enlargement or enhancement was found on either side of the neck; 6) bilateral caput humeralis and bilateral shoulder joints were normal. After treatment, the lesions disappeared, including those involving the bilateral shoulder joints, the multiple enlarged lymph nodes insubaxillary area, the recurrent and metastatic lesions at residual cavity after surgery of right paranasal sinus and nasal cavity. The multiple abnormal signals at bilateral hip joints and upper segment of the femur also disappeared.

Example 3. Treatment of Patient #3 with Small Cell Lung Cancer (SCLC) and Multiple Metastases Patient #3 was a 47 year old female. She was diagnosed with small-cell lung cancer at the right lung accompanied by multiple metastases in the liver, mediastinal lymph nodes, left humerus, left clavicle, vertebrae, right femur, pelvis, etc. Intramuscular injection and aerosol inhalation of SIFN and local spraying (on the skin over the bone metastases) of SIFN on lesions combined with chemotherapy were administered. After treatment, the primary lesions in the lung and the liver metastases apparently shrank. Also, part of the bone metastases was eliminated, such as those in the left humerus, left clavicle, C2 vertebra and left T9 processustransversus.

Regimens before administration of SIFN.

The first cycle of chemotherapy, Regimen CE, began on May 7, 2012, with each cycle lasting for 28 days: carboplatin (CBP), 300 mg/m$^2$ on day 1; etoposide (VP-16) at 100 mg/m$^2$ on days 3-7. Six cycles were completed by December 2012.

Administration of SIFN.

Treatment with SIFN began on May 28, 2012. Intramuscular injection of SIFN was applied every other day with 9 µg for the first time, 151 µg for the second time, and 18 µg for the third time and thereafter. Meanwhile, aerosol inhalation was administered at 600 µg each time per day. SIFN was simultaneously sprayed locally onto the skin surface of the left humerus, left clavicle, C2 vertebra, left T9 processus transversus and pelvis from Sep. 20, 2012, for 4-5 times per day. By December 2012, myelosuppression became apparent since SIFN treatment was applied in combination with chemotherapy. Hence, intramuscular injection and aerosol inhalation of SIFN was periodically provided, but local spraying of SIFN continued for another 3 months.

Diagnosis before administration of SIFN.

Chest CT scans on May 4, 2012 showed atelectasis in the upper lobe of the right lung, indicating a space-occupying lesion. A mass lesion was also seen in the right lobe of the liver with the maximum section area of 5.1 cm×6.7 cm. The boundary of the mass was obscure.

Test on tumor markers on May 7, 2012 displayed 171.40 ng/ml of CEA, 17.10 ng/ml of carbohydrate antigen 211 and 58.30 ng/ml of NSE.

Abdomen CT scan on May 8, 2012 showed multiple (at least 6) mass-like and nodular space-occupying lesions in both lobes of the liver. The biggest one among them was in the right anterior lobe, 54 mm×72 mm in size, heterogeneously enhanced, and made part of the liver capsule bulged. Other lesions had a diameter ranging from 9 mm to 12 mm. A small quantity of effusion existed around the liver. Diagnosis conclusion: multiple space-occupying masses were present in the liver, suggesting the possible occurrence of malignancy and metastases. A small amount of effusion was found around the liver.

PET/CT scans on May 9, 2012 showed FDG metabolism increased abnormally in multiple bones, left humerus, left clavicle, C2 vertebra, left T9 processus transversus, several segments of the pelvis and right femur were involved. The average SUV was 3.0 to 9.6. CT scan showed the structure disorder of the osseous substances in part of the lesions. The bilateral thoracic cavities were symmetrical, with the trachea in the middle. Consolidation were observed in the upper lobe of the right lung and partial of the consolidation region near the hilus of the lung showed mass-like shadow with elevated FDG metabolism having an average SUV of 7.8. The FDG metabolism in the consolidation region near the pleura appeared to be normal. Shadows of enlarged lymph nodes were seen at the mediastinum in front of the right side of the trachea, with relatively high FDG metabolism, which fused with shadow in the consolidation region, resulting an average SUV of 6.9. Diagnosis conclusion: 1) consolidation were found in the upper lobe of the right lung and the FDG metabolism in a portion near the hilus was abnormally high, suggesting the existence of a central lung cancer accompanied by atelectasis of the upper lobe of the right lung. Metastases of lymph nodes occurred at the mediastinum in front of the right side of the trachea. Multiple metastases were found in the liver and in the bones; 2) FDG metabolism was normal in the brain.

Diagnosis after administration of SIFN.

Color Doppler ultrasound scan on abdomen on Aug. 24, 2012 showed that the liver had regular shapes and the liver capsule was smooth. A solid mass of about 3.5 cm×2.8 cm (the previous size of which was 7.5 cm×5.9 cm) was found in the right lobe of the liver.

PET/CT scan on Oct. 9, 2012 showed: 1) the chest appeared to be symmetrical and the lung markings were clear. A lobulated mass of about 1.9 cm×1.8 cm in size was found in the rear segment of the right upper lobe, wherein the FDG intake was increased and the maximum value of SUV was 14.8. Abnormal shadows or metabolisms were not found in other parts of the lungs. The lymph nodes at the mediastinum and the right-sided hilum were enlarged with elevated FDG intakes ($SUV_{max}$=5.6). 2) the liver had normal shape, smooth edges, and normal ratio of the lobes. A low-density shadow of about 1.9 cm×2.7 cm (the previous size of which was 7.5 cm×5.9 cm) was found in the lower segment of the anterior lobe of the right liver. The FDG intakes at outer margins were increased with $SUV_{max}$ being 3.5. 3) The cervical vertebrae, thoracic vertebrae and lumbar vertebrae were well arranged. Bone substances were destroyed focally in the left ilium and the right femoral intertrochanter, wherein the FDG intakes were elevated with $SUV_{max}$ being 4.5. (Bone metastases previously existed in the left humerus, left clavicle, C2 vertebra, left T9 processus transversus, several segments of the pelvis and the right-sided femur.) After treatment with SIFN, the primary lesions in lung and the metastases in the liver evidently shrank. Also, bone metastases were eliminated in the left humerus, left clavicle, C2 vertebra and the left T9 processus transversus.

Example 4. Treatment of Patient #4 with Adenocarcinoma and Multiple Bone Metastases Patient #4 was a 30 year old female diagnosed with adenocarcinoma of the left lung, accompanied by multiple bone metastases including the eighth rear rib on the right side, right-sided sacroiliac joint, left-sided ilium, etc. SIFN administration by intramuscular injection, aerosol inhalation and local spraying on lesions combined with chemotherapy and radiotherapy were provided. After treatment, lesions in lung evidently shrank and the SUV value decreased according to PET/CT. Lesion in the left pubis turned better after local spraying of the interferon. Bone metastases in the fifth and eighth thoracic vertebrae disappeared.

Regimens before administration of SIFN.

Chemotherapy was carried out from Jun. 28, 2011 (GP regimen): 1.6 g of Gemzar on days 1 and 8 and 60 mg of Cisplatin on days 1 and 2.

Regimens for administration of SIFN in combination with chemotherapy and radiotherapy.

Treatment of SIFN began on Jul. 1, 2011. Intramuscular injection of SIFN was provided every other day with 15 µg for the first time and 18 µg for the second time and thereafter. Meanwhile, aerosol inhalation was administered every day, once per day with 600 µg for each time. Spraying was locally applied to the skin surfaces of the left pubis, the fifth and eighth thoracic vertebrae and the eighth rear rib on the right side from Jun. 12, 2012, at 4 to 5 times per day. Surgery with Cyberknife was performed to the right ilium near the sacroiliac joint on Jul. 17, 2012.

Diagnosis before administration of SIFN.

The physical examination result of May 2011 showed shadows in the lungs. Chest CT scan on Jun. 16, 2011 displayed a round-shaped space-occupying shadow in the rear segment of the left lower lobe. The shadow was slightly enhanced with a size of 31.8 mm×36.8 mm. Needle biopsy of the left lung on Jun. 22, 2011 showed a few abnormal cells. Liquid based cytology demonstrated the existence of adenocarcinoma cells. Bone scan on Jun. 27, 2011 showed abnormal radioactive concentrations in the eighth rear rib on the right side, the right-sided sacroiliac joint and the left-sided ilium, suggesting possible metastases in the pelvis and ribs.

Diagnosis after administration of SIFN.

PET/CT scans on Sep. 22, 2011 showed a shadow of a lobulated soft tissue at the lower lobe of the left lung, 3.2 cm×2.5 cm in size. FDG intakes were increased with an average value of SUV of 4.7 and a maximum value of 5.3. Chest CT scan on Feb. 1, 2012 showed that the exudate shadows in both lungs disappeared as compared to the images taken on Aug. 23, 2011. The lesions on the rear segment of the right upper lobe disappeared and a mass of 21 mm×15 mm was found in the posterior segment of the left lower lobe. The lesions at the lower lobe of the left lung evidently shrank in size, compared to those on Aug. 23, 2011.

PET/CT scans on Jul. 14, 2012 showed an irregular low-density shadow of 3.3 cm×2.1 cm at the left lower lobe adjacent to the pleura, in which spot-like calcification could be seen. FDG intakes were slightly and unevenly elevated, with the maximum value of SUV 2.1. Bone scan on Sep. 14, 2012 showed that the radioactive concentration did not change much in eighth rear rib on the right side, right-sided sacroiliac joints, left-sided ilium, left pubis and right-sided iliac joint, compared to the images taken on Jun. 11, 2012. However, the metastatic lesions at the fifth and eighth thoracic vertebrae disappeared as shown in the images of Jun. 11, 2012.

MR of sacroiliac joints on Sep. 21, 2012 showed that the lesions in the left pubis turned better as compared to the images taken on Jun. 27, 2011. The lesions in the right ilium adjacent to the sacroiliac joint, the right-sided femoral head and neck further progressed.

The treatment lasted for more than one year until December 2012. The lesions in the lungs evidently shrank in size and the SUV values decreased according to PET/CT. As for the bone metastases, the lesions at the right ilium adjacent to the sacroiliac joint worsened after radiotherapy. However, lesions in the left pubis and the fifth and eighth thoracic vertebrae exhibited obvious improvement after 3 months of local spraying of SIFN.

Example 5. Treatment of Patient #5 with Nasopharyngeal Carcinoma

Patient #5 was a 48 year old female who was first diagnosed as having low-differentiated squamous nasopharyngeal carcinoma, IVa (T4N3M0) on Dec. 27, 2007.

Administration of SIFN began on: SIFN was administered on Oct. 30, 2012, at a dose of 15 µg each time, every other day (subcutaneous or intramuscular injection). Patient did not have any surgery or any adjuvant therapy. Treatment regimen included nasopharyngeal spraying of the SIFN administered as of Nov. 24, 2012. The injecting dosage of SIFN-co increased to 21 µg as of Nov. 25, 2012.

The medical history of Patient #5 was collected on Oct. 30, 2012, as follows:

Patient's chief complaints: Nasopharyngeal carcinoma was diagnosed more than 4 years ago, followed by radiotherapy and chemotherapy more than 3 years ago. Recurrence of the tumor had been found for more than 1 week ago.

Patient's Medical History: A mass was found at the neck in 2007 when the patient referred to Jinshan Hospital affiliated to Fudan University, to get further examination. The pathological examination on Dec. 27, 2007 revealed an undifferentiated type of non-keratinizing carcinoma in the nasopharynx, with immunohistochemistry results showing CK+, EMA+, LCA−, CD68−, 34β E12+, CK5/6+. No other relevant examination and treatment was performed thereafter. The mass relapsed at the neck in 2009 and the patient had an examination in Mianyang Central Hospital on May 8, 2009. A few atypical hyperplastic squamous epithelia were found in nasopharyngeal mucosa. The patient was suggested to have a biopsy again. Examination on May 12, 2009 showed chronic inflammation with few suspected cancer cells at the margin. Another examination was made in West China Hospital on May 16, 2009, which showed hyperplasia of squamous epithelia acompanied with focal coagulative necrosis, slight to moderate atypical hyperplasia of squamous epithelia, and some inflammatory exudate. After diagnosis, the patient went to Mianyang Tumor Hospital and had 35 courses of radiotherapy and 5 doses of chemotherapy in total. The lesions at nasopharynx and the mass at the neck disappeared after the treatment, suggesting clinical remission.

The patient complained of head discomfort again in March, 2012, with no obvious abnormality found after examinations. A CT scan was performed on Jun. 11, 2012 due to the recurrent headache. The results showed that the right-sided wall was thickened in nasopharynx and local ulcers were likely developed. No treatment was given at the time. The biopsy examination on Oct. 23, 2012 showed a few degenerated atypical cells amidst the chronically inflammated mucous, suggesting the possibility of low differentiated squamous cell carcinoma. The CT scan imaging on Oct. 26, 2012 showed irregular mass of soft tissues density at the left side of the top wall of the nasopharynx.

The main symptoms of this patient currently related to the headache at the right side and difficulty in moving joints of her jaw. She had to stay at home. The patient and her relatives volunteered to use SIFN as of Oct. 30, 2012.

The course of SIFN treatment: On Oct. 31, 2012, the patient had her first intramuscular injection of SIFN of 15 μg at 10:00 am on Oct. 30, 2012. One hour after the administration, the patient shivered, and her body temperature reached 37.8° C. after 4 hours. The temperature then decreased and became normal about 7 hours after the drug administration. Her waist and lower extremities began to ache more than 8 hours after the drug administration, which disappeared the next morning. She had no other complaints.

The patient had her second intramuscular injection of SIFN of 15 μg at 14:00 pm on Nov. 1, 2012. The patient shivered about 6 hours after the drug administration. The highest body temperature as measured was 38.0° C. (the specific time was not recorded). The body temperature then decreased and finally became normal, without any drug administration or other solutions to reduce the body temperature. Meanwhile, headache was reported, which was ameliorated the next morning. She had no other complaints.

The patient had her fourth intramuscular injection of SIFN of 15 μg on Nov. 6, 2012. The patient shivered about 3 hours after the drug administration. Then, her body temperature began to increase and reached the highest (38.0° C.) after 5 hours since the drug administration. The temperature become normal 2 hours later without any attempts to decrease the body temperature. Meanwhile, a headache, a toothache, an earache and a stomach discomfort were reported, which were ameliorated the next morning. She had no other complaints.

The patient had her ninth intramuscular injection of SIFN of 15 μg on Nov. 15, 2012. The patient shivered for about 3 hours after the drug administration. Then, her body temperature reached 37.4° C. after about 6 hours since the drug administration and began to decrease later. Meanwhile, a headache, a toothache and an earache were reported, which were ameliorated the next morning. No other discomforts were reported.

A blood routine on Oct. 26, 2012 the following results: WBC, $5.1 \times 10^9$/L; PLT, $353 \times 10^9$/L; percentage of lymphocyte, 28.5%; percentage of neutrophilic granulocyte, 59.4%; and percentage of monocytes, 8.3%. A blood routine on Nov. 6, 2012 showed the following results: WBC, $4.1 \times 10^9$/L; PLT, $234 \times 10^9$/L; percentage of lymphocyte, 40.7%; percentage of neutrophils, 50.6%. A liver function test on Nov. 13, 2012 showed that ALT was 18 U/L and AST was 17 U/L. A CT scan on Nov. 19, 2012 showed that the mass at the top wall of nasopharynx was a little bit larger in size, compared to one found in CT scan on Oct. 26, 2012. The patient reported that her persistent headache was evidently relieved, while she still had difficulty in moving joints of her jaw and neck pain. She had no other complaints. The therapeutic regimen was adjusted as follows based on her situation. Specifically, the intramuscular injection of rIFN was adjusted to 21 Lg each time, every other day, combined with local spraying of SIFN on the nasopharynx.

Spraying was applied to the nasopharynx from Nov. 24, 2012 for 5-6 times per day. The right-side teeth ached about 2 to 3 minutes after the drug administration and the pain was ever severer than before. The pain persisted for about 2 hours and then substantially disappeared. Intramuscular injection of SIFN of 21 gig began on Nov. 25, 2012. No chills, fever or headache was reported.

The patient had an intramuscular injection of SIFN of 21 Lg for the fourth time on Dec. 1, 2012, combined with nasopharyngeal spraying. She shivered for about 4 hours after the drug administration but the body temperature remained normal. The toothache still existed but was much better than before. The secretion of the nasopharynx contained a little blood. No obvious headache occurred. The patient was suggested to have a blood routine and a liver function test.

The patient had an intramuscular injection of SIFN of 21 Lg for the tenth time on Dec. 13, 2012, combined with nasopharyngeal spraying. Toothache and earache were still reported after the drug administration but not as bad as before. Her waist ached sometimes and the secretion of the nasopharynx contained a little blood. No other discomfort was reported. The patient was suggested to pay attention to the secretion of the nasopharynx and prevent the debris from blocking the airway.

The blood routine on Dec. 4, 2012 showed the following results: WBC, $4.4 \times 10^9$/L; PLT, $201 \times 10^9$/L. The liver function test on Dec. 5, 2012 showed that ALT was 48 U/L and AST was 49 U/L. The patient still had a toothache and paroxysmal pains appeared at the left ear 7 days ago (the ache appeared at the right ear before). The secretion of the nasopharynx remained the same. No headache was reported.

Jan. 23, 2013: The patient said the headache and toothache were gone and felt that she was able to move her jaw better. The secretion of the nasopharynx remained the same. She had no other complaints.

Example 6. The Use of a Transdermal Patch in the Treatment of Melanocarcinoma A transdermal patch having an effective amount of SIFN in the range of about 200 microgram to about 600 microgram per patch is applied on a subject's cancerous skin lesions, such as a melanocarcinoma lesion. The subject has no metastasis. No other anti-tumor therapy is provided. Subcutaneous injection and/or intramuscular injection of SIFN are/is administered combined with the application of the transdermal patch on the cancerous lesions. Specifically, the subcutaneous injection and/or intramuscular injection are/is provided every other day at 15 microgram to 24 microgram of interferon per dose. The transdermal patch is replaced with a new one every day. This treatment regimen is continued for a duration of 2 months. Tumor shrinkage is expected.

Example 7. The Use of a Spray in the Treatment of Tongue Cancer

SIFN is administered to a subject who has a projecting mass at his tongue which can be highly to moderately differentiated squamous cell carcinoma. The subject can have enlarged lymph nodes at his neck. No other anti-tumor therapy is provided. Briefly, the SIFN is administered by subcutaneous injection and/or intramuscular injection as well as local administration by spraying on the projecting mass. The subcutaneous injection and/or intramuscular injection are/is provided every other day with 9 microgram to 24 microgram of the interferon per dose. The spray containing an effective amount of interferon of in the range of about 200 microgram/ml to about 600 microgram/ml is applied to the lesions on his tongue 2 to 4 times per day. Also, interferon can be injected to the lymph nodes at the neck once every three days at about 80 microgram to about 200 microgram of interferon per dose. Administration of the SIFN is continued for about 20 days. The mass on the tongue is expected to fall off and the enlarged lymph nodes are expected to shrink in size.

---

What is claimed is:

1. A method of treating both a primary tumor and a secondary bone cancer that has metastasized from the primary tumor in a subject, comprising administering to the subject an effective amount of an anti-cancer interferon, wherein the interferon comprises the amino acid sequence of SEQ ID NO: 1.

2. The method of claim 1, wherein the interferon is administered locally to the subject.

3. The method of claim 1, wherein the interferon is administered to a cancerous lesion, or to an area affected by cancer or comprising cancer cells.

4. The method of claim 1, wherein the interferon is administered via at least one of: infiltration administration, percutaneous administration, transdermal administration, epidermal administration, and transmucosal administration.

5. The method of claim 1, wherein the interferon is administered to or on a bone, a skin, a mucosa, and/or a submucosa of the subject at a concentration in a range of 0.01 mg/ml to 5 mg/ml.

6. The method of claim 1, wherein the interferon is administered by spraying.

7. The method of claim 1, wherein the interferon is administered to or on a skin in proximity to the bone affected by cancer, or to or on a skin surrounding the bone affected by cancer.

8. The method of claim 1, wherein the interferon is administered to a mucosa in proximity to the bone affected by cancer, or to a mucosa surrounding the bone affected by cancer.

9. The method of claim 1, wherein the interferon is administered locally in a dose range of 2 micrograms to 2100 micrograms.

10. The method of claim 6, wherein the effective amount of interferon is 6 micrograms to 100 micrograms per spray.

11. The method of claim 1, wherein the interferon is formulated for local administration as at least one of: a dry powder, an aqueous solution, a cream, a membrane permeation or diffusion drug delivery system, a controlled release drug delivery system, a closed drug delivery system, a transdermal patch, and a depot comprising the interferon to be injected under the skin, for producing a slow-release effect.

12. The method of claim 1, wherein the interferon is formulated as nanoparticles, microparticles, microspheres, liposomes or a controlled release single or composite material.

13. The method of claim 1, wherein the interferon is administered systemically and/or by inhalation.

14. The method of claim 1, further comprising administering to the subject at least one other anti-cancer therapy before, at about the same time, and/or after administration of the interferon.

15. The method of claim 14, wherein the at least one other anti-cancer therapy comprises at least one of: chemotherapy, radiotherapy, surgical therapy, interventional therapy, biotherapy, targeted therapy, and Traditional Chinese medicine.

16. The method of claim 15, wherein the biotherapy comprises at least one of gene therapy and immunotherapy, and the surgical therapy comprises ablation therapy.

17. A method of treating both a primary tumor and a secondary bone cancer that has metastasized from the primary tumor in a subject, comprising administering to the subject an effective amount of an anti-cancer interferon, wherein the interferon comprises the amino acid sequence of SEQ ID NO: 1, and wherein the primary tumor is selected from the group consisting of bone cancer, skin cancer, subcutaneous carcinoma, mucosal carcinoma and submucosal carcinoma.

18. The method of claim 17, wherein the interferon is administered percutaneously on or to the skin of the subject, or transmucosally to or on the mucosa of the subject.

19. The method of claim 17, further comprising administering to the subject at least one other anti-cancer therapy before, at about the same time, and/or after administration of the interferon.

20. A method of treating both a primary tumor and a secondary bone cancer that has metastasized from the primary tumor in a subject, comprising administering to the subject an effective amount of an anti-cancer interferon, wherein the interferon comprises the amino acid sequence of SEQ ID NO: 1, and wherein the primary tumor is selected from the group consisting of non-small-cell lung cancer (NSCLC), small-cell lung cancer (SCLC), melanoma, and adenocarcinoma.

* * * * *

SEQUENCE LISTING

```
<160> NUMBER OF SEQ ID NOS: 3

<210> SEQ ID NO 1
<211> LENGTH: 167
<212> TYPE: PRT
<213> ORGANISM: Artificial Sequence
<220> FEATURE:
<223> OTHER INFORMATION: Amino acid sequence of recombinant interferon

<400> SEQUENCE: 1

Met Cys Asp Leu Pro Gln Thr His Ser Leu Gly Asn Arg Arg Ala Leu
1               5                   10                  15

Ile Leu Leu Ala Gln Met Arg Arg Ile Ser Pro Phe Ser Cys Leu Lys
            20                  25                  30

Asp Arg His Asp Phe Gly Phe Pro Gln Glu Glu Phe Asp Gly Asn Gln
        35                  40                  45

Phe Gln Lys Ala Gln Ala Ile Ser Val Leu His Glu Met Ile Gln Gln
    50                  55                  60

Thr Phe Asn Leu Phe Ser Thr Lys Asp Ser Ser Ala Ala Trp Asp Glu
65                  70                  75                  80

Ser Leu Leu Glu Lys Phe Tyr Thr Glu Leu Tyr Gln Gln Leu Asn Asp
                85                  90                  95

Leu Glu Ala Cys Val Ile Gln Glu Val Gly Val Glu Glu Thr Pro Leu
            100                 105                 110

Met Asn Val Asp Ser Ile Leu Ala Val Lys Lys Tyr Phe Gln Arg Ile
        115                 120                 125

Thr Leu Tyr Leu Thr Glu Lys Lys Tyr Ser Pro Cys Ala Trp Glu Val
    130                 135                 140

Val Arg Ala Glu Ile Met Arg Ser Phe Ser Leu Ser Thr Asn Leu Gln
145                 150                 155                 160

Glu Arg Leu Arg Arg Lys Glu
                165

<210> SEQ ID NO 2
<211> LENGTH: 504
<212> TYPE: DNA
<213> ORGANISM: Artificial Sequence
<220> FEATURE:
```

```
<223> OTHER INFORMATION: Nucleotide sequence encoding recombinant
      interferon

<400> SEQUENCE: 2
atgtgcgacc tgccgcagac ccactccctg ggtaaccgtc gtgctctgat cctgctggct      60
cagatgcgtc gtatctcccc gttctcctgc ctgaaagacc gtcacgactt cggtttcccg     120
caggaagaat cgacggtaa ccagttccag aaagctcagg ctatctccgt tctgcacgaa      180
atgatccagc agaccttcaa cctgttctcc accaaagact cctccgctgc ttgggacgaa     240
tccctgctgg aaaaattcta caccgaactg taccagcagc tgaacgacct ggaagcttgc     300
gttatccagg aagttggtgt tgaagaaacc ccgctgatga acgttgactc catcctggct     360
gttaaaaaat acttccagcg tatcaccctg tacctgaccg aaaaaaaata ctccccgtgc     420
gcttgggaag ttgttcgtgc tgaaatcatg cgttccttct ccctgtccac caacctgcag     480
gaacgtctgc gtcgtaaaga ataa                                            504

<210> SEQ ID NO 3
<211> LENGTH: 504
<212> TYPE: DNA
<213> ORGANISM: Artificial Sequence
<220> FEATURE:
<223> OTHER INFORMATION: Nucleotide sequence encoding recombinant
      interferon

<400> SEQUENCE: 3
tacacgctgg acggcgtctg ggtgagggac ccattggcag cacgagacta ggacgaccga      60
gtctacgcag catagagggg caagaggacg gactttctgg cagtgctgaa gccaaagggc     120
gtccttctta agctgccatt ggtcaaggtc tttcgagtcc gatagaggca agacgtgctt     180
tactaggtcg tctggaagtt ggacaagagg tggtttctga ggaggcgacg aaccctgctt     240
agggacgacc tttttaagat gtggcttgac atggtcgtcg acttgctgga ccttcgaacg     300
caataggtcc ttcaaccaca acttctttgg ggcgactact tgcaactgag gtaggaccga     360
caatttttta tgaaggtcgc atagtgggac atggactggc ttttttttat gaggggcacg     420
cgaacccttc aacaagcacg actttagtac gcaaggaaga gggacaggtg gttggacgtc     480
cttgcagacg cagcatttct tatt                                            504
```